(12) United States Patent
Shirai et al.

(10) Patent No.: US 10,030,240 B2
(45) Date of Patent: Jul. 24, 2018

(54) TWO-DIMENSIONAL CELL ARRAY DEVICE AND APPARATUS FOR GENE QUANTIFICATION AND SEQUENCE ANALYSIS

(71) Applicant: Hitachi, Ltd., Chiyoda-ku, Tokyo (JP)

(72) Inventors: Masataka Shirai, Tokyo (JP); Hideki Kambara, Tokyo (JP); Kiyomi Taniguchi, Tokyo (JP); Maiko Tanabe, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 14/771,339

(22) PCT Filed: Mar. 12, 2013

(86) PCT No.: PCT/JP2013/056818
§ 371 (c)(1),
(2) Date: Aug. 28, 2015

(87) PCT Pub. No.: WO2014/141386
PCT Pub. Date: Sep. 18, 2014

(65) Prior Publication Data
US 2016/0010078 A1    Jan. 14, 2016

(51) Int. Cl.
*C12N 15/10* (2006.01)
*C12Q 1/6874* (2018.01)
(Continued)

(52) U.S. Cl.
CPC .... *C12N 15/1003* (2013.01); *B01L 3/502761* (2013.01); *B01L 7/52* (2013.01);
(Continued)

(58) Field of Classification Search
CPC ... C12Q 1/68; C12M 1/34; B01L 3/50; C40B 50/06
See application file for complete search history.

(56) References Cited

U.S. PATENT DOCUMENTS

| | | | |
|---|---|---|---|
| 2003/0077611 A1* | 4/2003 | Slepnev | C12Q 1/6809 435/6.14 |
| 2009/0098541 A1 | 4/2009 | Southern et al. | |

(Continued)

FOREIGN PATENT DOCUMENTS

| | | |
|---|---|---|
| CN | 102639716 A | 8/2012 |
| JP | 2007-89566 A | 4/2007 |

(Continued)

OTHER PUBLICATIONS

International Search Report (PCT/ISA/210) dated May 28, 2013, with English translation (Five (5) pages).

(Continued)

*Primary Examiner* — Narayan Bhat
(74) *Attorney, Agent, or Firm* — Crowell & Moring LLP

(57) ABSTRACT

In order to conduct gene expression analysis of a number of genes in a number of cells, it has been necessary to separate cells, extract genes therefrom, amplify nucleic acids, and perform sequence analysis. However, separation of cells imposes damages on the cells, and it requires the use of an expensive system. Gene expression analysis in each cell can be carried out with high accuracy by arranging a pair of structures comprising a cell trapping section and a nucleic acid trapping section in a vertical direction to extract individual genes in relevant cells, synthesizing cDNA in the nucleic acid trapping section, amplifying nucleic acids, and analyzing the sequences using a next-generation sequencer.

14 Claims, 19 Drawing Sheets

(51) Int. Cl.
*B01L 3/00* (2006.01)
*B01L 7/00* (2006.01)

(52) U.S. Cl.
CPC ....... *C12N 15/1096* (2013.01); *C12Q 1/6874* (2013.01); *B01L 2200/0631* (2013.01); *B01L 2200/0668* (2013.01); *B01L 2200/10* (2013.01); *B01L 2300/0636* (2013.01); *B01L 2300/0819* (2013.01); *B01L 2300/0851* (2013.01); *B01L 2300/0864* (2013.01); *B01L 2300/1805* (2013.01); *B01L 2400/0421* (2013.01)

(56) References Cited

U.S. PATENT DOCUMENTS

| | | |
|---|---|---|
| 2010/0240041 A1 | 9/2010 | Matsunaga et al. |
| 2012/0245053 A1 | 9/2012 | Shirai et al. |

FOREIGN PATENT DOCUMENTS

| | | |
|---|---|---|
| JP | 2008-539711 A | 11/2008 |
| WO | WO 00/55363 A2 | 9/2000 |
| WO | WO 2009/016842 A1 | 2/2009 |
| WO | WO 2011/068088 A1 | 6/2011 |
| WO | WO 2012/170560 A2 | 12/2012 |

OTHER PUBLICATIONS

Taniguchi, et al. "Quantitative analysis of gene expression in a single cell by qPCR", Nature Methods, vol. 6, No. 7, 2009, pp. 1-4, (Seven (7) pages).
White, et al. "High-throughput microfluidic single-cell Rt-qPCR", Proceedings of the National Academy of Sciences, vol. 108, No. 34, 2011, pp. 13999-14004 (Six (6) pages).
Yin, et al. "Microfluidics for single cell analysis", Current Opinion in Biotechnology 2012, vol. 23, No. 1, pp. 110-119, (Ten (10) pages).
Hsiao, et al. "Microfluidic Device for Capture and Isolation of Single Cells", Proc. of SPIE vol. 7759, 2010, pp. 77590W1-77590W9 (Ten (10) pages).
Lindstroem, S. et al. "Overview of single-cell analyses: microdevices and applications", The Royal Society of Chemistry, Lab Chip, 2010, vol. 10, No. 24, pp. 3363-3372, (Eleven (11) pages).
Extended European Search Report issued in counterpart European Application No. 13878277.6 dated Nov. 2, 2016 (3 pages).
Chinese-language Office Action issued in counterpart Chinese Application No. 201380073998.1 dated Nov. 11, 2016 4 pages).
Chinese-language Office Action issued in counterpart Chinese Application No. 201380073998.1 dated Dec. 21, 2017 (2 pages).
Zhang et al., "Elaboration of Microfluidic Biochip for Cancer Cell Gene Expression Analysis", Journal of Integration, Jul. 2012, pp. 46-49, vol. 1, No. 2 with English abstract.

\* cited by examiner

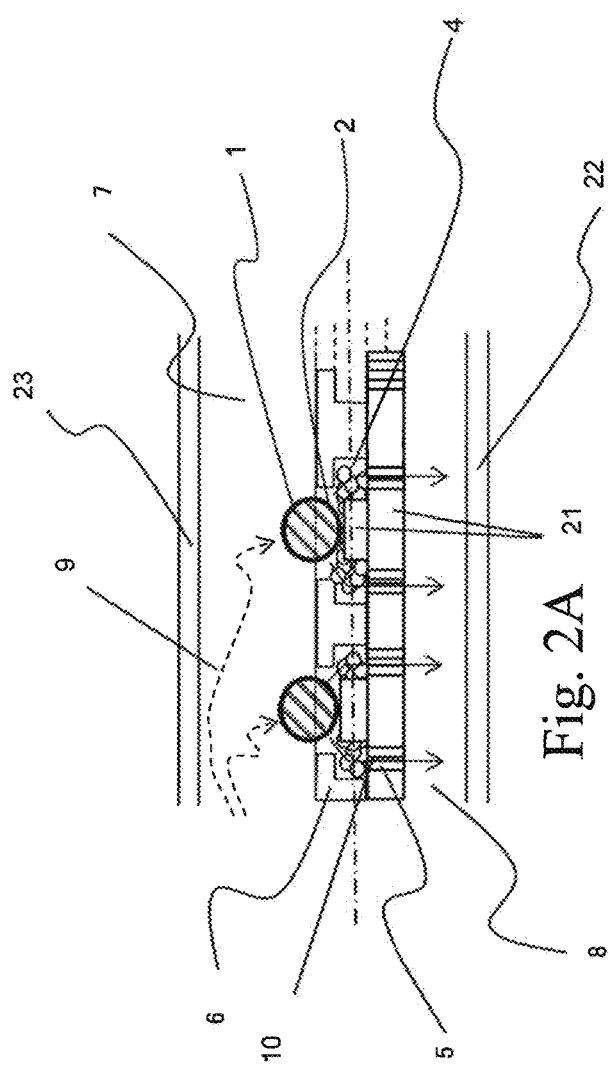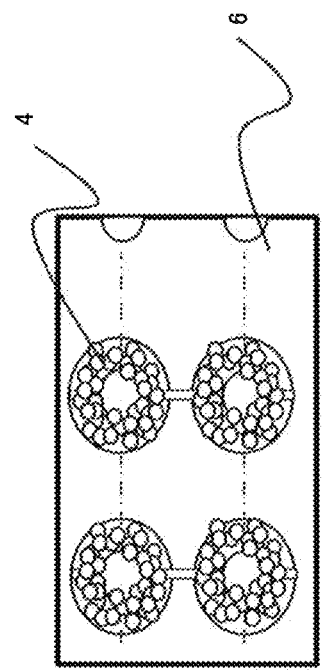

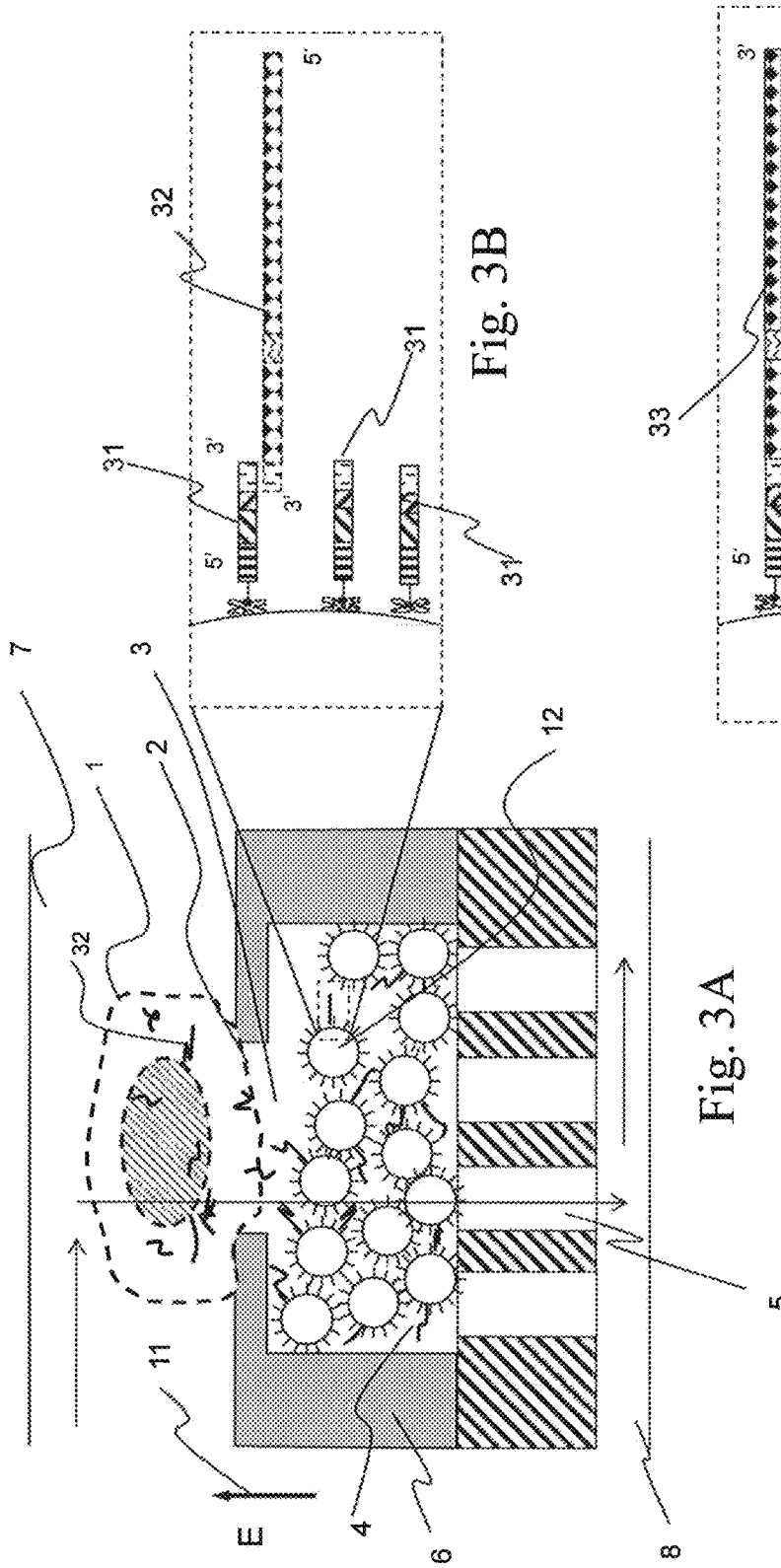
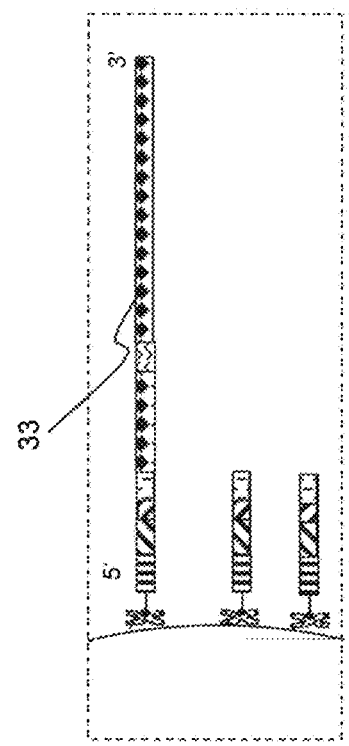
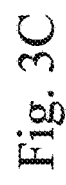
Fig. 3A
Fig. 3B
Fig. 3C

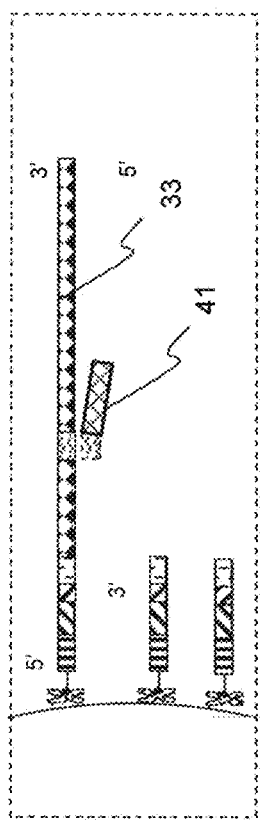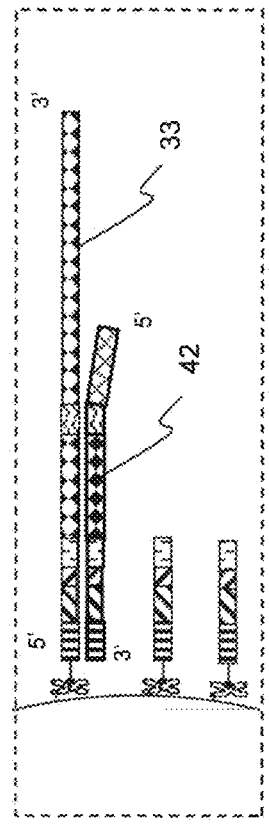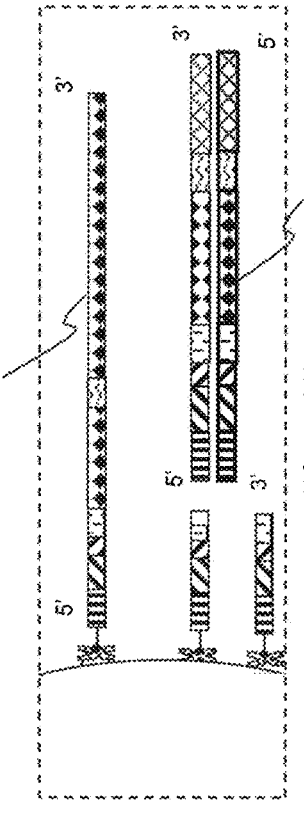

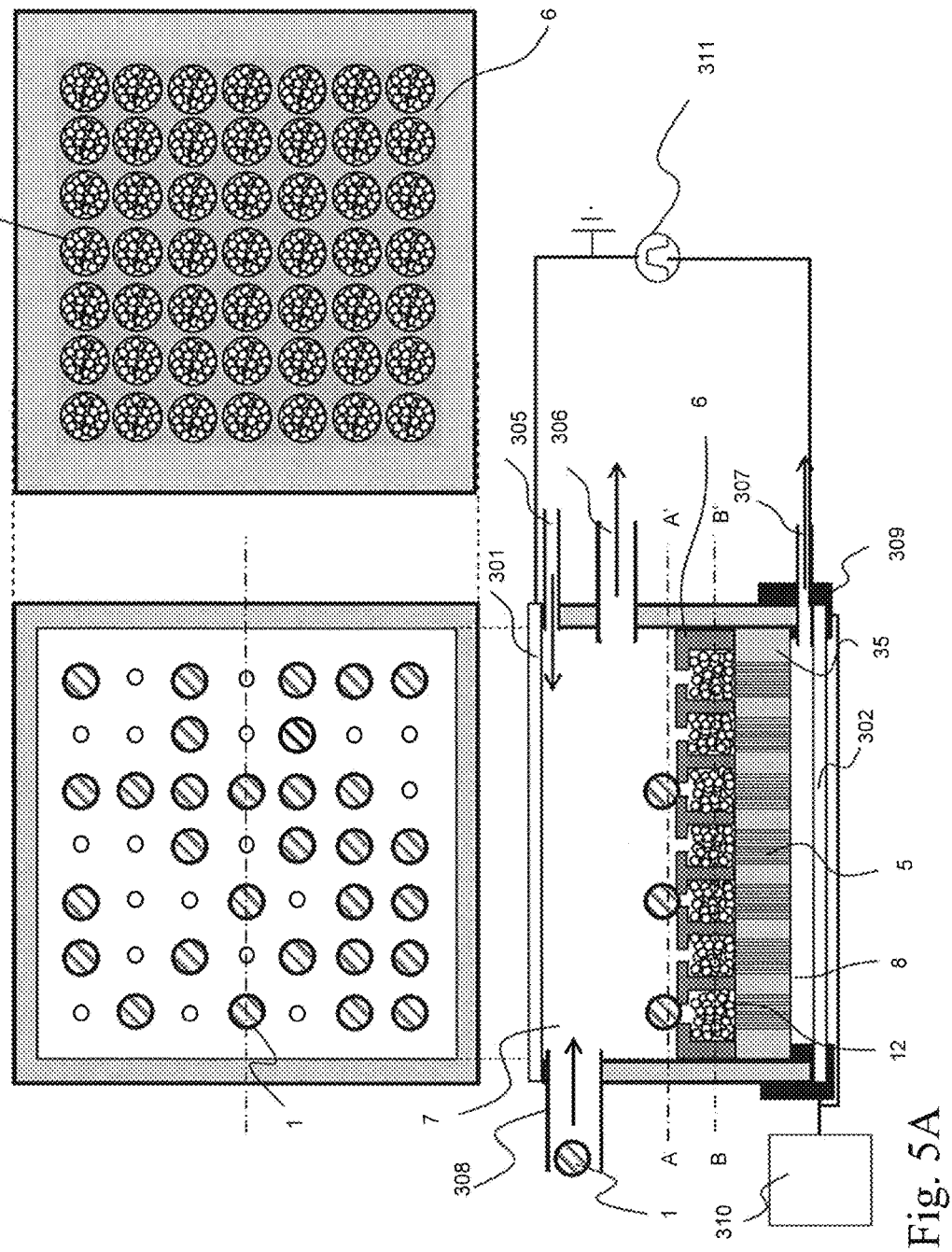

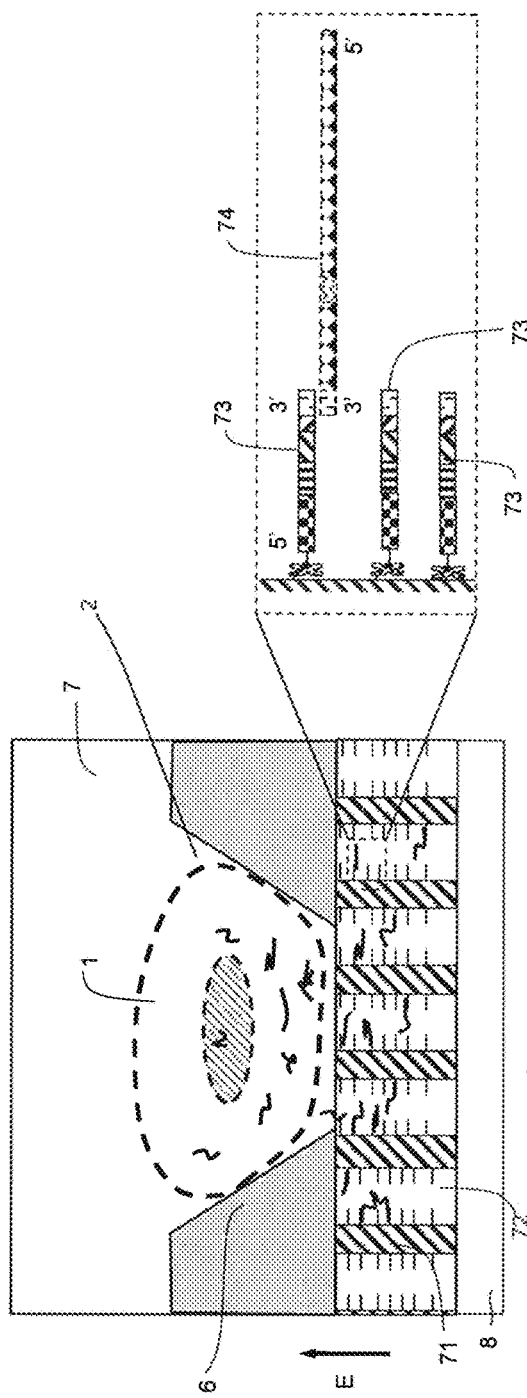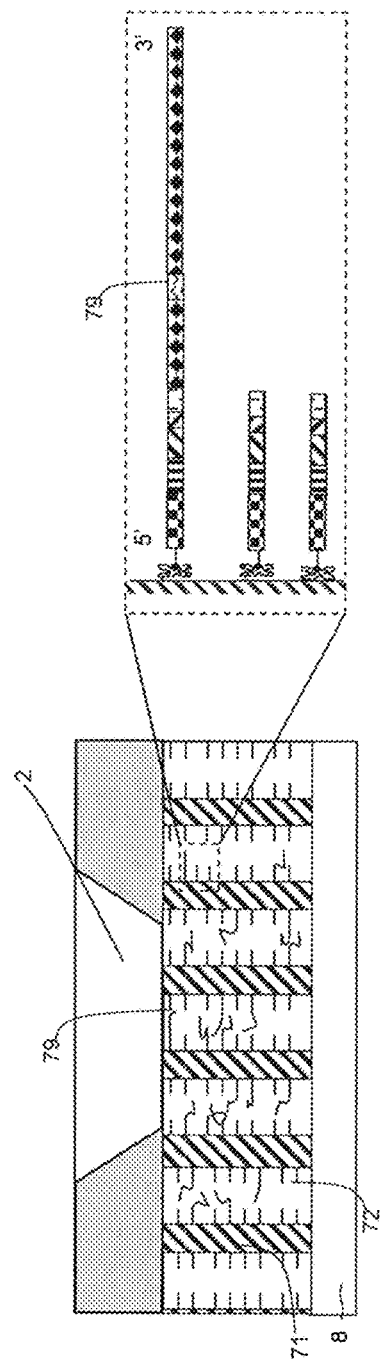
Fig. 7A
Fig. 7B

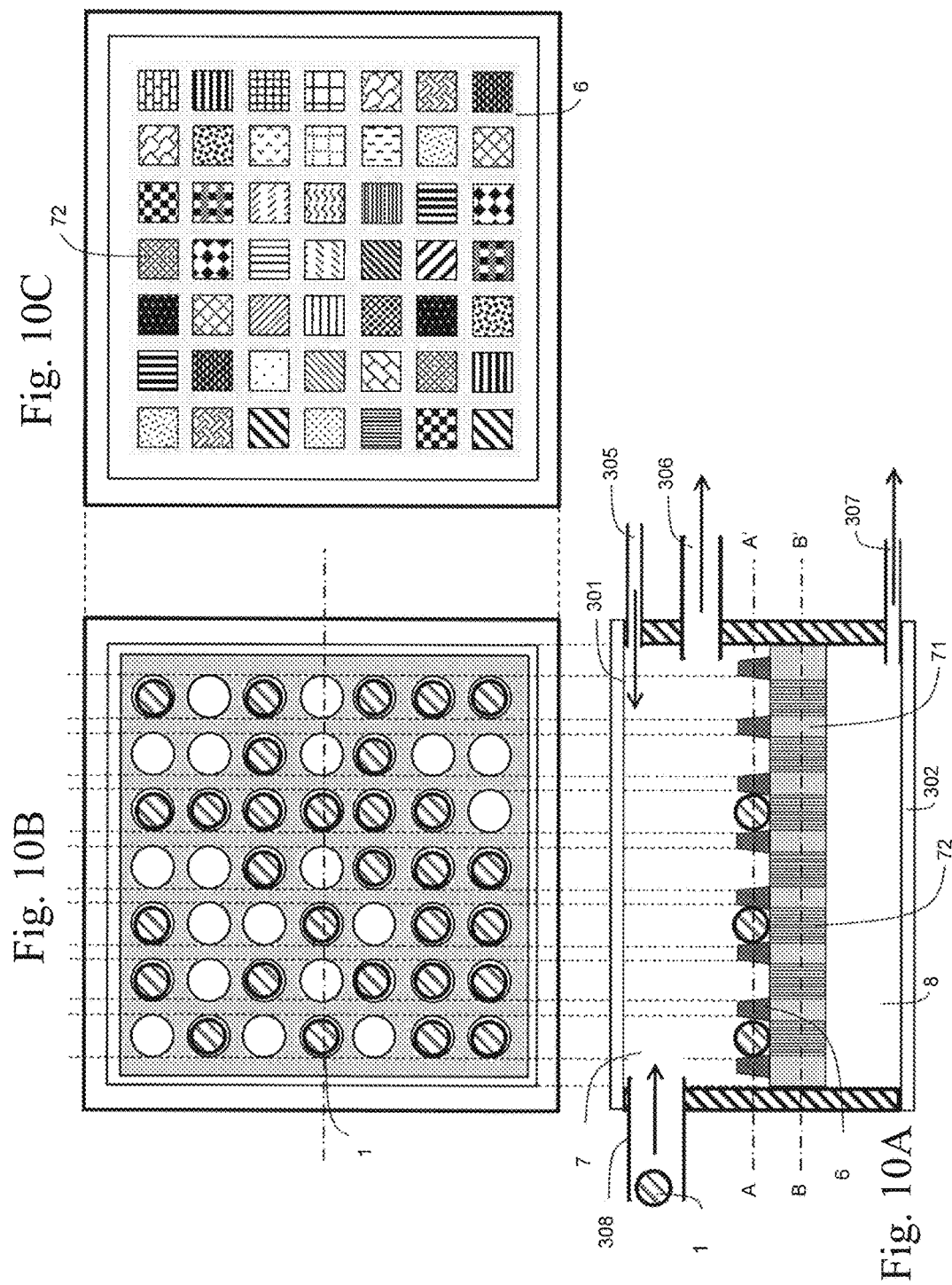

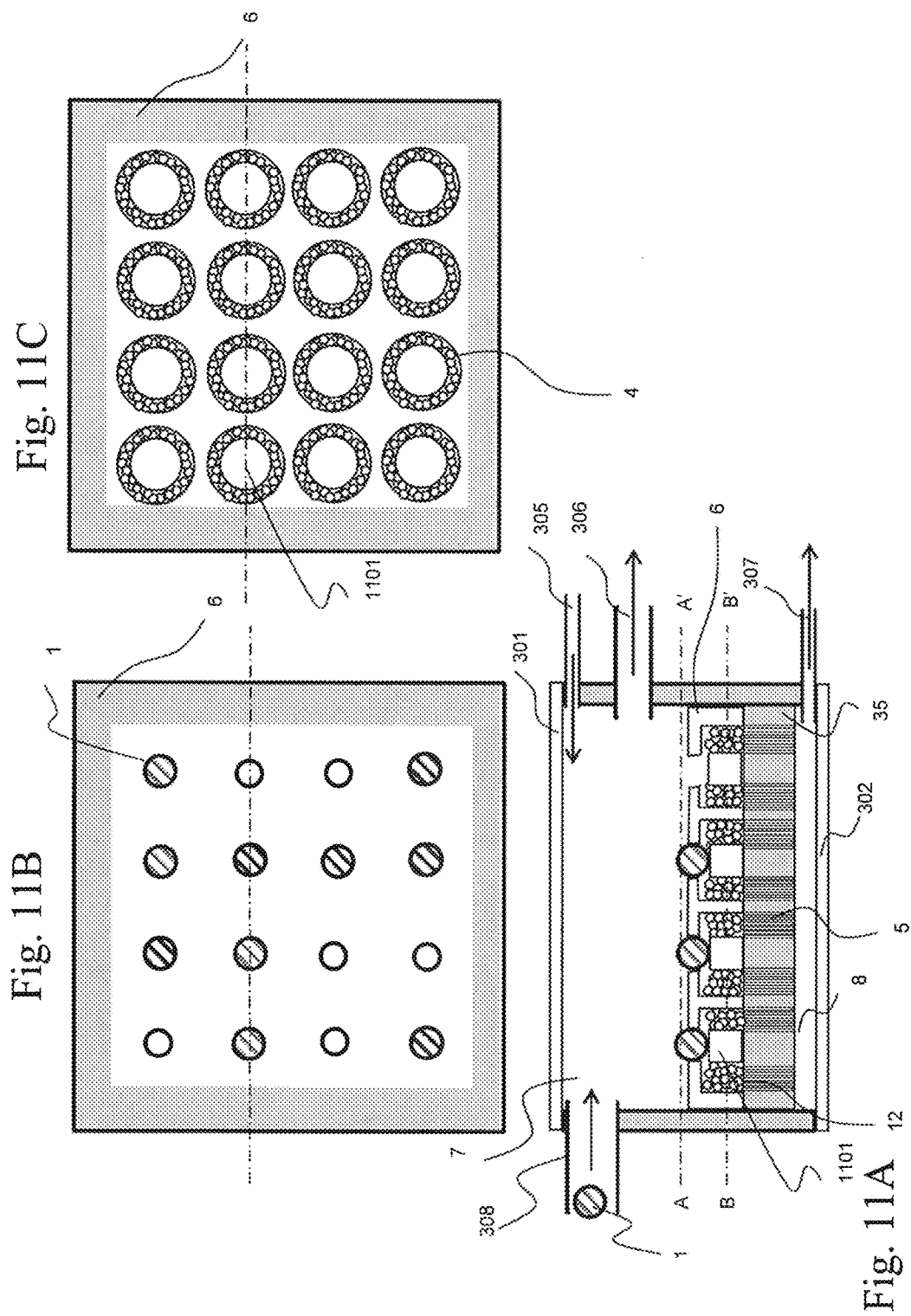

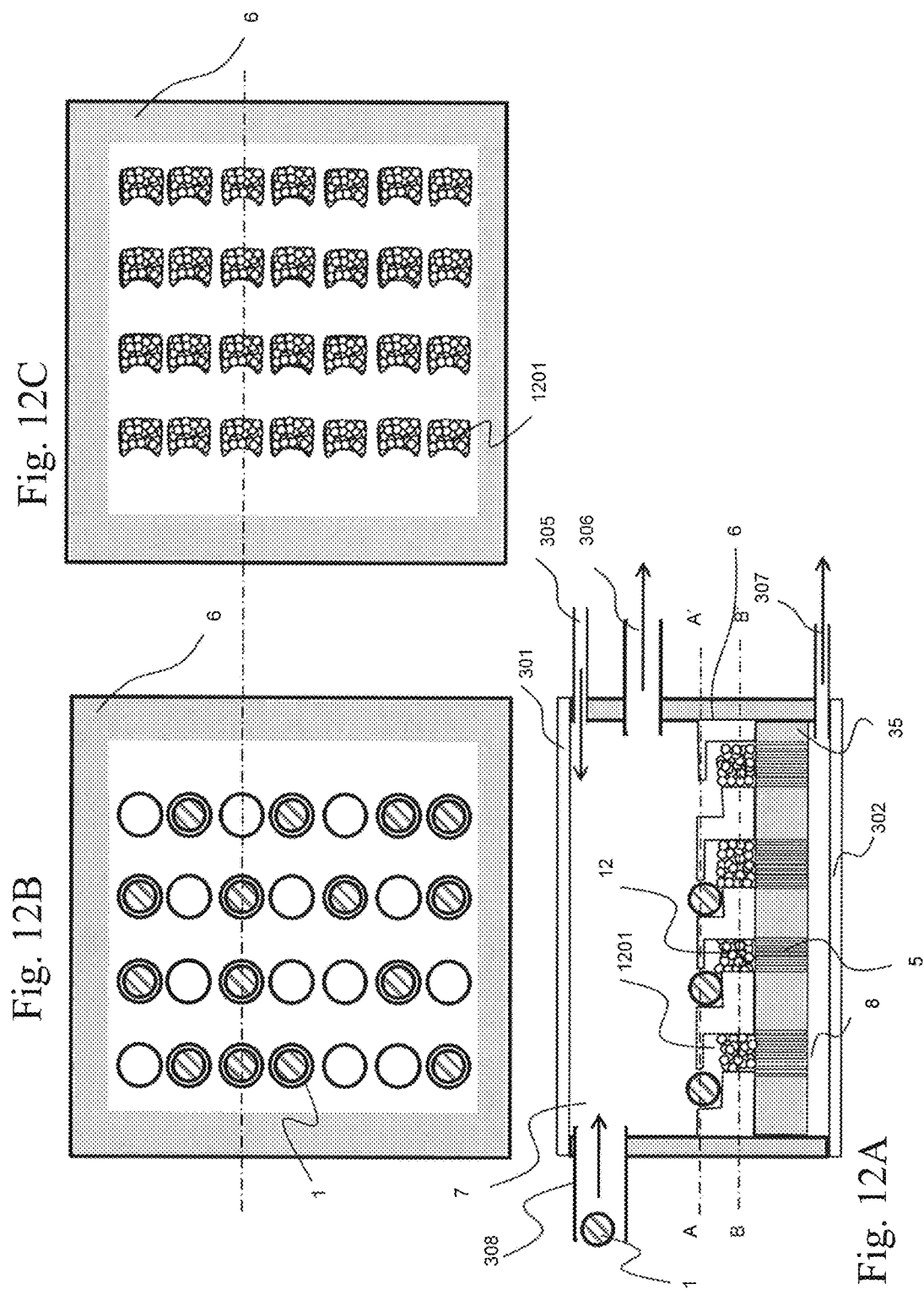

TWO-DIMENSIONAL CELL ARRAY DEVICE AND APPARATUS FOR GENE QUANTIFICATION AND SEQUENCE ANALYSIS

TECHNICAL FIELD

The present invention relates to methods for gene expression analysis, cell function analysis, biological tissue analysis, disease diagnosis, drug discovery, and the like. More particularly, the present invention relates to a method for mRNA analysis at the single-cell level.

BACKGROUND ART

Gene expression analysis is carried out by extracting mRNA from cells, preparing a complementary strand thereof; i.e., cDNA, increasing its copy number via PCR, and capturing the target at a relevant probe position using a DNA probe array (DNA chip) to detect it on the basis of fluorescence. PCR amplification or a method involving the use of a DNA chip, however, is disadvantageous in terms of the low accuracy of quantitative analysis. Accordingly, development of a method for analyzing gene expression profiles with high accuracy has been awaited. Along with the completion of human genome analysis, the demand for quantitative gene expression analysis is increasing. In recent years, however, a method comprising extracting mRNA from a single cell and quantitatively analyzing it has been needed. An example of a method of analysis with high quantitative efficiency is quantitative PCR. This method of quantitative analysis comprises preparing a standard sample with the same DNA sequence as the target, performing PCR amplification under the same conditions, and observing and comparing the progression of amplification using fluorescent probes. When the target is a single cell, the number of existing mRNA is small, and quantitative analysis is difficult to conduct. When expression of a plurality of genes is to be quantitatively analyzed, samples are divided and independently subjected to quantitative analysis. When the number of target genes is large and expression levels of some genes are low, accordingly, analysis may be sometimes impossible to conduct as a result of sample division.

Under the above circumstances, the inventors developed a method comprising converting all mRNA into cDNA, preparing a cDNA library retained on beads (i.e., a cDNA population including all cDNA), and using it for quantitative analysis. They demonstrated that errors in determination of genes expressed at very low levels caused by sample division could be eliminated with the repeated use of a cDNA library and expression levels of a plurality of genes contained in a single cell could be accurately determined (Non-Patent Document 1: Nature Method, Vol. 6, No. 7, 2009, pp. 503-506).

In the method described above, all the processes, including mixing of a reaction reagent with a sample-containing solution and purification, are performed manually. From the viewpoint of fractionation accuracy and solvent evaporation, the volume of the reaction solution is limited to at least several hundreds nanoliters to microliters. This necessitates the use of a reagent at an adequate concentration even when a single cell is to be analyzed. Accordingly, the amount of a reaction reagent (i.e., the number of moles) increases in proportion to the reaction volume, which in turn increases reagent cost. When assay of numerous cells is necessary in order to achieve statistically significant data, the reagent cost would be very high. Accordingly, a method that can he carried out with a reduced reaction volume and solves problems in fractionation accuracy and evaporation has been desired.

In order to overcome the aforementioned problems, a method involving the use of a device comprising small flow channels referred to as "microfluidics" in combination was adopted in the past. An example in which microfluidics is employed for single cell analysis is described in Non-Patent Document 2 (Proceedings of the National Academy of Sciences, Vol. 108, No. 34, 2011, pp. 13999-14004). FIG. 1 of Non-Patent Document 2 shows the constitution of a device in which a chip is composed of 300 unit structures, so that 300 cells can be simultaneously treated. 3×50 such unit structures are arranged on a chip, a unit structure is horizontally long, a sample solution flows in a longitudinal direction, and the reaction is successively carried out while the sample solution continues to flow. The reaction volume is 10 nL at the time of reverse transcription and it is 50 nL at the time of PCR. That is, the reaction volume is reduced.

In order to simultaneously treat a large number of cells, in addition, it is necessary to simultaneously subject many cells to gene expression analysis in a cost-effective manner. To this end, a method in which a cDNA library is constructed with the use of porous membranes instead of beads is described in Patent Document 1 (JP 2009-276883 A). This method involves the use of a device that obtains two-dimensional distribution of gene expression and implements gene expression analysis of many cells. When genes in a single cell are subjected to expression analysis with the use of such device, it is not necessary to isolate cells. Thus, mRNA can be directly extracted from cells originating from biological tissue sections and can be subjected to gene expression analysis. In order to increase the number of genes that can be analyzed, however, it was necessary to perform fluorescence assay or chemiluminesence assay repeatedly, in proportion to the number of genes assayed.

SUMMARY OF THE INVENTION

Object to be Solved by the Invention

For regenerative medicine, diagnosis with the use of genes, or basic understanding of vital phenomena, quantitative analysis of each cell constituting tissue is considered to be important in addition to quantitative analysis of the average gene expression level in tissue. In addition to thorough analysis of each extracted cell, it is necessary to quantify biological matter in many cells in order to attain statistically significant data. In particular, quantitative monitoring of expression levels of various genes is desired. In such a case, biological matter to be quantified is mRNA in a cell. For simplicity, genes are considered to correspond to mRNA at a ratio of 1:1, and gene expression quantification is considered to be the same as mRNA quantification. In general, the term "gene expression assay" is used in a broader sense. In such a case, the presence of a plurality of mRNA variations (variants) read from a single gene locus and various controls in the process of mRNA maturation or translation into a protein should be taken into consideration at the time of assay, and target substances to be assayed increase according to need. For simplification of description, the term indicates quantification of mature mRNA herein.

The number of mRNAs corresponding to genes expressed in a single cell may be from approximately several molecules to several tens of thousands of molecules. In order to accurately quantify mRNAs corresponding to genes with small numbers of molecules, it is necessary to convert mRNAs into forms that can be quantified efficiently. Accurate quantification of expression levels of a plurality of genes became possible by constructing a cDNA library derived from a single cell with high efficiency (80% or higher) on the surface of beads described in Non-Patent Document 1 (Nature Method, Vol. 6, No. 7, 2009, pp. 503-506) and repeatedly assaying the cDNA library. Because the number of repetition is limited to approximately 10 to 20, the number of genes that can be assayed is also limited to 10 to 20. The number of cells that can be simultaneously assayed is not more than approximately 100, and the cost required for reagents is very high. Accordingly, a technique that enables assay of a number of as large a number of genes as necessary for many cells is important at the industrial level.

In order to implement gene expression analysis in a single cell, it is necessary that cells be isolated and introduced into separate reaction wells. It is also necessary that reagents for cell disruption, reverse transcription, and PCR amplification to be fractionated to reaction wells. This necessitates the use of a robot for fractionation in order to perform analysis automatically, and the size and the cost of the analyzer increase.

When mRNA is extracted from cells via microfluidics and nucleic acid is amplified in order to eliminate the need for fractionation conducted by a robot, in addition, reaction channels should be aligned in line. Accordingly, the chip size increases in proportion to the number of lines, the size of the microfluidic device increases, and the cost of the device increases.

As shown in the lower left part of FIG. 1 of Non-Patent Document 2 (Proceedings of the National Academy of Sciences, Vol. 108, No. 34, 2011, pp. 13999-14004), in practice, the target cells of analysis are introduced into the leftmost reaction tank and the cells are disrupted. Subsequently, the sample solution is transferred to the right reaction tank, reverse transcription is allowed to proceed, the sample solution is transferred rightward, and PCR is carried out. Thus, the sample is treated while allowing the sample to move in one direction on a plane. At the end, the treated sample is recovered from the rightmost tank. When microfluidics is employed, a solution needs to migrate on the substrate plane, and the footprint of the unit structure becomes large. In addition, a chip area is used for fluid channels through which samples or reagents are introduced into unit structures or for fluid channels through which the treated samples are discharged. Accordingly, the chip area increases as the number of sequences of a unit structure increases, and the cost of a chip is elevated.

According to Non-Patent Document 2 (Proceedings of the National Academy of Sciences, Vol. 108, No. 34, 2011, pp. 13999-14004), the proportion of mRNAs relative to all mRNAs in the cells that can be treated, assayed, and quantified as samples is unknown. In order to quantify biochemical substances such as mRNAs at the time of single-cell analysis, it is critical that target molecules (mRNAs, in particular) be efficiently assayed. For example, a small number of mRNAs; that is, approximately 10 or fewer molecules of mRNAs in a single cell, should be assayed. If the number of molecules of samples treated to be assayed decreases, a substantive measurement error (a sampling error in accordance with the Poisson distribution) would occur.

Patent Document 1 (JP 2009-276883 A) discloses a method involving the use of a cDNA library sheet in order to simultaneously subject many cells to gene expression analysis in a cost-effective manner. While many cells can be collectively assayed, it was necessary to repeat fluorescence assays using a cDNA library in order to increase the number of genes that could be analyzed. Thus, the number of genes to be analyzed was limited.

Means for Solving the Object

In order to attain the objects described above, and more specifically, in order to provide a device or apparatus that is capable of simultaneously assaying an increased number of cells and efficiently treating molecules in a cell (mRNAs herein) in a cost-effective manner, the device or apparatus according to the present invention is constructed as described below.

Cells are immobilized at given positions, mRNAs as target molecules to be quantified are extracted from nucleic acids, and unit structures that can perform sample treatment such as reverse transcription and cDNA library construction for each cell are two-dimensionally arranged. A cell-derived sample flows in a direction perpendicular to a planar device surface, and a unit structure is provided on a chip surface, so as to reduce the area of the chip accounted for by the unit structure. A tag sequence (a tag molecule) is introduced during sample treatment, so that the position of the unit structure can be identified by analyzing the sample even when the treated sample is mixed and recovered with the unit structure provided on the plane. This can eliminate the need for the provision of mechanisms for sample recovery for each unit structure.

Specifically, the present invention includes the following.
(1) A device for nucleic acid extraction comprising:
a cell trapping section for immobilizing a single cell;
a fluid channel in which an extraction solution for extracting a nucleic acid from the cell flows downward through the cell trapping section;
a nucleic acid trapping section connected to the cell trapping section via the fluid channel and located downstream of the cell trapping section, the nucleic acid trapping section being capable of immobilizing the extracted nucleic acid; and
a fluid channel that discharges the solution after nucleic acid extraction from the nucleic acid trapping section in a direction opposite from the cell trapping section,
wherein the cell trapping section, the two fluid channels, and the nucleic acid trapping section are paired in a vertical direction and a plurality of such pairs are arranged in a planar direction.
(2) The device for nucleic acid extraction according to (1), wherein the nucleic acid trapping section comprises beads on which DNA for nucleic acid trapping is immobilized.
(3) The device for nucleic acid extraction according to (1), wherein the nucleic acid trapping section comprises a porous membrane comprising DNA for nucleic acid trapping immobilized on pores.
(4) The device for nucleic acid extraction according to any of (1) to (3), wherein the cell trapping section comprises a substance immobilized thereon that chemically binds to a substance on a cell surface.
(5) The device for nucleic acid extraction according to (2) or (3), wherein some DNA for nucleic acid trapping described above each comprise a sequence for identifying a position on a chip.
(6) The device for nucleic acid extraction according to (2) or (3), wherein some DNA for nucleic acid trapping described above comprise separate sequences for the trapped nucleic acid molecules.

(7) The device for nucleic acid extraction according to (6), which comprises a means for introducing an enzyme for reverse transcription of RNA trapped by the nucleic acid trapping section.
(8) The device for nucleic acid extraction according to any of (1) to (7), wherein a region immediately downstream of the cell trapping section is made of an optically transparent material.
(9) The device for nucleic acid extraction according to any of (1) to (8), wherein a nucleic acid trapping section is provided in a region immediately downstream of the cell trapping section.
(10) The device for nucleic acid extraction according to any of (1) to (8), wherein a nucleic acid trapping section is provided in a region other than the region immediately downstream of the cell trapping section.
(11) An apparatus for nucleic acid treatment, comprising: the device for nucleic acid extraction according to any of (1) to (10); and a means for introducing a reagent for constructing a cDNA library.
(12) An apparatus for nucleic acid treatment, comprising: the device for nucleic acid extraction according to any of (1) to (10); a reagent for constructing a cDNA library; and a means for introducing a reagent for nucleic acid amplification.
(13) An apparatus for nucleic acid treatment, comprising: the device for nucleic acid extraction according to any of (1) to (10); and a microscope section for observing cells trapped by the cell trapping section under a differential interference microscope, phase contrast microscope, Raman microscope, or Coherent Raman microscope.
(14) A method for extracting a nucleic acid from a cell using a device for nucleic acid extraction comprising a cell trapping section and a nucleic acid trapping section provided downstream of the cell trapping section, the method comprising:

bringing cells into contact with the cell trapping section so as to allow the cell trapping section to trap (capture) each cell;

allowing an extraction solution for extracting a nucleic acid from the cell to flow downward through the cell trapping section in a fluid channel;

immobilizing the extracted nucleic acid to the nucleic acid trapping section; and discharging the solution after nucleic acid extraction from the nucleic acid trapping section in a direction opposite from the cell trapping section through a fluid channel, wherein the device for nucleic acid extraction comprises the cell trapping section, the two fluid channels, and the nucleic acid trapping section which are paired in a vertical direction and a plurality of such pairs arranged in a planar direction.

Effects of the Invention

The present invention provides a device or apparatus that quantifies biological molecules such as nucleic acids in a single cell, determines the sequences, or identifies biological molecule types, and such device or apparatus is capable of measuring an increased number of cells at a time and efficiently treating molecules in the cells (e.g., mRNAs) in a cost-effective manner.

BRIEF DESCRIPTION OF THE DRAWINGS

FIGS. 2A and 2B schematically show the device for nucleic acid extraction according to an embodiment of the present invention.

FIGS. 3A-3C schematically show the device for nucleic acid extraction according to an embodiment of the present invention.

FIGS. 4D-4F schematically show a method of using the device for nucleic acid extraction according to an embodiment of the present invention.

FIGS. 5A-5C schematically show the device for nucleic acid extraction according to an embodiment of the present invention.

FIGS. 7A and 7B schematically show the device for nucleic acid extraction according to an embodiment of the present invention.

FIGS. 10A-10C schematically show the device for nucleic acid extraction according to an embodiment of the present invention.

FIGS. 11A-11C schematically show the device for nucleic acid extraction according to an embodiment of the present invention.

FIGS. 12A-12C schematically show the device for nucleic acid extraction according to an embodiment of the present invention.

EMBODIMENTS FOR CARRYING OUT THE INVENTION

Figures 1A, 1B:
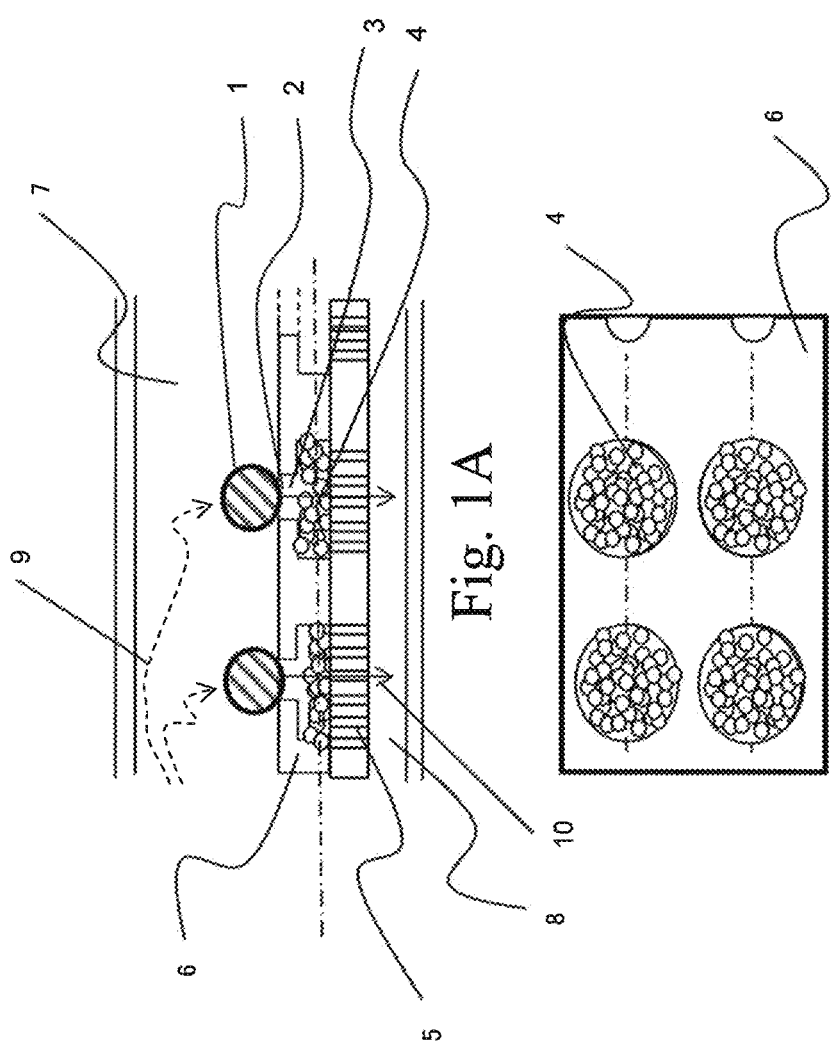
FIGS. 1A and 1B schematically show the device for nucleic acid extraction according to an embodiment of the present invention.

An example of a specific structure of the device for nucleic acid extraction according to the present invention is shown in FIG. 1. FIG. 1(a) shows a cross section taken in a direction perpendicular to the planar device surface and FIG. 1(b) shows a cross section taken along a dot-and-dash line shown in the above figure in a direction parallel to the plane. In the cell trapping section 2 that immobilizes cells 1 that have been introduced into the device one by one (the cell trapping section has pores each immobilizing cells in FIG. 1), the fluid channel 3 in which the extraction solution for extracting a nucleic acid from the cell s downward through e cell trapping section, a nucleic acid trapping section 4 connected to the cell trapping section via the fluid channel and located downstream of the cell trapping section, which immobilizes the extracted nucleic acid thereon, and a fluid channel 5 that discharges the solution after nucleic acid extraction from the nucleic acid trapping section in a direction opposite from the cell trapping section. The cell trapping section, the two fluid channels, and the nucleic acid trapping section are paired in a vertical direction, and a plurality of such pairs are arranged in a planar direction. A device for nucleic acid extraction as described above is a basic structure according to the present invention. This structure is provided on the planar substrate 6 and inside thereof. According to need, the upper reaction region 7 for introducing cells and the lower reaction region 8 for discharging the treated nucleic acid may be added. The dotted arrow 9 indicates an example of tracing of cell migration and the arrow 10 indicates the direction of migration of the nucleic acid extracted from cells and the treated sample.

The device described in Non-Patent Document 2 (Proceedings of the National Academy of Sciences, Vol. 108, No. 34, 2011, pp. 13999-14004) comprises a cell capture chamber (cell trapping section), a reverse transcription (RT) chamber, and a qPCR chamber on a plane. Such device is required to have two different types of reaction chambers that are larger than area required for cell trapping, and a valve for liquid flow regulation and a fluid channel must be provided on a plane. Accordingly, the area on the device to be provided with a unit structure for single-cell treatment (a structure associated with single-cell treatment en comprising a cell capture chamber, an RT chamber, a qPCR chamber, and a fluid channel in the structure described in Non-Patent Document 2 (Proceedings of the National Academy of Sciences, Vol. 108, No. 34, 2011, pp. 13999-14004)) is increased disadvantageously. Since device cost is roughly proportional to device area, device cost is increased as the number of cells that are simultaneously treated increases.

In order to overcome the problems described above, according to an embodiment shown in FIG. 1, a nucleic acid trapping section is provided immediately below a cell rapping section, a cDNA library is constructed using the extracted nucleic acids in the nucleic acid trapping section, and the library is subjected to the subsequent treatment. Thus, a plurality of reactions can be implemented in a single reaction region.

It may be preferable that the nucleic acid trapping section be packed with many beads or it have a porous structure in order to improve nucleic acid capture (trapping) efficiency. By increasing the surface area of a reaction field in a unit volume, reaction can be carried out in a small reaction tank with high efficiency within a short period of time.

When conducting nucleic acid amplification with the use of the constructed cDNA as a template via PCR or transcription on the device, collecting the samples, and subjecting the samples to quantification via sequencing using a next-generation sequencer, in addition, the constructed cDNAs are modified to have different sequences depending on the positions of capture (trapping). By subjecting a solution of collected samples to sequencing, accordingly, the cell from which the expression level of a gene derived can be identified.

This can eliminate the need of isolation of the unit structure or provision of a valve mechanism or a fluid channel for regulation of sample migration.

In the structure shown in FIG. 1, a reagent necessary for the nucleic acid trapping section 4 may be supplied from the upper reaction region 7 for performance of PCR in the nucleic acid trapping section, and the PCR amplification product may be collected from the lower reaction region 8. It may be preferable that a mechanism that adjusts the temperature of the entire device to a level adequate for a PCR cycle be provided outside the device.

In order to assay the cellular conditions in advance using a non-invasive microscope and quantify the biological substance in the same cell via gene expression analysis, for example, a nucleic acid trapping section may not be provided in a region immediately below a region in which cells are immobilized, but it may be provided in the vicinity of such region in a more preferable structure.

An example of a specific structure is shown in FIG. 2. FIG. 2(a) shows a cross section taken in a direction perpendicular to the planar device surface and FIG. 2(b) shows a cross section taken along a dot-and-dash line shown in the above figure in a direction parallel to the plane. In order to perform microscopic observation prior to nucleic acid extraction from the cell 1, regions 21, 22, and 23 in the device are made of optically transparent materials. Microscopic observation can be carried out with the use of, for example, a transmission microscope, differential interference microscope, phase contrast microscope, or Coherent anti-Stokes Raman scattering spectroscope (CARS microscope).

After the completion of microscopic observation, the sample and the reagent are allowed to flow in a direction indicated by an arrow 10 so as to enable performance of nucleic acid extraction and reverse transcription. Sample treatment may be carried out in the same manner as the treatment conducted without microscopic observation.

EXAMPLES

Example 1

This example relates a device for nucleic acid extraction in which a nucleic acid trapping section is constructed by packing a lot of DNAs (DNA probes) for nucleic acid trapping which are immobilized on beads, and an apparatus for sample treatment.

The basic constitution of the unit structure of the device for nucleic acid extraction in this example is the same as that shown in FIG. 1. However, the device in this example is constituted to be capable of constructing cDNA library, in addition to extracting nucleic acid from cells and capturing mRNA, and using it as a template, this device makes it possible to obtain a sufficient amount of nucleic acid amplification products having known sequences at the terminuses that can be subjected to sequencing.

FIG. 3(a) shows a cross section of a unit structure for treating a single cell in the device for nucleic acid extraction corresponding to this example. FIG. 3 and FIG. 4(b) to (f) show concepts of steps that can be performed with the use of the device: step (b) of nucleic acid extraction from the captured cells and nucleic acid (mRNA) capture; step (c) of cDNA synthesis; steps (d) and (e) of nucleic acid amplification (PCR) and synthesis of the 2nd strands into which known terminal sequences necessary for sequencing have been added; and step (f) of PCR amplification. FIG. 5 shows the structure of the entire device for nucleic acid extraction. FIG. 5(a) shows a cross section of the entire device for nucleic acid extraction corresponding to FIGS. 1(a) and 3(a), and FIG. 5(b) shows a cross section taken along the line A-A' shown in FIG. 5(a), which corresponds to FIG. 1(b). FIG. 5(c) shows a cross section corresponding to the cross section taken along the line BB' shown in FIG. 5(a).

Subsequently, the operations of the device for nucleic acid extraction are described in accordance with the procedure. In FIG. 3(a), a solution is allowed to flow through the cell trapping section from the upper reaction region 7 toward the lower reaction region 8, so as to immobilize cells 1 suspended in the solution in a particular region (the cell trapping section (opening)) 2 of the device. Cells migrate along with the flow of the solution and reach the cell trapping section. Since the size of the opening of the cell trapping section is smaller than the diameter of cells, the cells are immobilized thereto. The captured cells serve as stoppers for the solution flow, and the solution accordingly migrates to a cell trapping section that has not captured any cells. Thus, remaining cells migrate to regions that have not captured any cells and they are then captured. When a desired number of cells 1 are captured, a solution that is allowed to flow to the upper reaction region 7 is replaced with an extraction solution for extracting a nucleic acid, such as a lysis buffer, used for disrupting cells (e.g., a mixture of a surfactant such as Tween 20 and a protease). At the same time, an electric field is applied in direction 11 to allow nucleic acids (mRNAs) in the cells to migrate to the nucleic acid trapping section 4 via electrophoresis. The nucleic acid trapping section 4 is a region between the fluid channel 3 connecting the nucleic acid trapping section 4 to the cell trapping section 2 and the fluid channel 5 connecting the nucleic acid trapping section 4 to the lower reaction region 8, which is packed with beads 12 on which DNA probes 31 for nucleic acid capture have been immobilized.

FIG. 3(b) shows an enlarged diagram of the bead surface 12 on which the DNA probes 31 have been immobilized. The electric field 11 is applied to mRNAs 32 extracted from cells, so that mRNAs 32 are captured by beads in the nucleic acid trapping section located immediately below the captured cells. In order to conserve the positional information of the cells where the captured mRNAs were present as the sequence information, the DNA probes 31 immobilized on beads comprise different sequences depending on the position of the nucleic acid trapping section; that is, a cell recognition sequence. The 3' terminus of the DNA probe 31 comprises a poly (T) sequence, which hybridizes to a poly (A) sequence at the 3' terminus of mRNA to capture mRNA. The nucleic acid trapping sections 4 positioned on the two-dimensional arrays shown in FIG. 1(b) and FIG. 5(c) are packed with beads on which the DNA probes 31 comprising different cell recognition sequences are immobilized.

According to this example, a sequence structure of the DNA probe 31 for mRNA capture is slightly more complicated. As shown in FIG. 3(b), the DNA probe 31 comprises, from the 5' terminus, a 30-bp universal sequence for PCR amplification (in the forward direction), a 5-bp cell recognition tag sequence, a molecule recognition tag sequence comprising a 15-bp random sequence, and an 18-bp oligo (dT) sequence+a 2-bp VN sequence. By adding the universal sequence for PCR amplification to the DNA probe 31, the resultant can be used as a universal primer in the subsequent step of PCR amplification. A cell recognition tag can recognize $4^5=1,024$ single cells in the case of, for example, a 5-bp random sequence. Specifically, cDNA libraries can be simultaneously prepared from 1,024 single cells, and the cell origin can be identified on the basis of the sequence information attained with the use of a next-generation sequencer, as described above. By adding the molecule recognition tag sequence (e.g., a 7-bp sequence) to the DNA probe 31, in addition, $4^7=1.6\times10^4$ molecules can be identified. On the basis of the DNA sequence information concerning the amplification product attained with the use of a next-generation sequencer, accordingly, the molecule origin of an amplification product with the same cell origin and the same gene sequence can be identified. More specifically, amplification bias between genes generated in the process of amplification can be corrected, and the amount of mRNA that was present in the sample at the beginning can be quantified with high accuracy. When the expression level of the same gene in a single cell is greater than the level of variations of molecule recognition tag sequences, however, the accuracy of amplification bias correction is lowered. The oligo (dT) sequence located in the position closest to the 3' terminus is used to hybridize to the poly (A) tail added to the 3' side of mRNA 32 to capture mRNA 32 (FIG. 3(b)).

In this example, a poly (T) sequence is used in a part of the DNA probe 31 for mRNA capture, in order to analyze mRNA. In order to perform microRNA or genome analysis, random sequences may be used as a part of a sequence complementary to the sequence to be analyzed instead of the poly (T) sequence.

Subsequently, mRNA 32 captured by the DNA probe 31 on heads is used as a template to synthesize the 1st cDNA strand 33. In this process, the gaps of the packed beads are tilled with a solution containing a reverse transcriptase and a synthetic substrate, temperature is slowly increased to 50° C., and complementary strand synthesis is then carried out for approximately 50 minutes (FIG. 3(c)). After the completion of the reaction, RNase is allowed to flow through a region packed with beads so as to degrade and remove mRNA 32. Subsequently, a solution containing an alkali denaturant and a wash solution are allowed to flow through the gaps between beads, and the remaining substances and the degraded products are removed. On the beads that have been introduced into the nucleic acid trapping section up to this point in the process, arrays of the cDNA library as shown in FIG. 5(c) are constructed while reflecting the positions of the cells captured by the cell trapping section.

Subsequently, a lysis buffer is allowed to flow from the lower reaction region 8 toward the upper reaction region 7, in order to remove cell fragments remaining in the cell trapping section. A plurality of (up to 100 types of) target-gene-sequence-specific primers 41 to which the universal sequence for PCR amplification (Reverse) had been added are allowed to anneal to the 1st cDNA strand (FIG. 4(d)), so as to synthesize the 2nd cDNA strand 42 via complementary strand elongation (FIG. 4(e)). That is, the 2nd cDNA strand is synthesized under multiplex conditions. Thus, double-stranded cDNA strands comprising universal sequences for amplification (forward/reverse) at both terminuses, and cell recognition tags, molecule recognition tags, and gene-specific sequences are synthesized for a plurality of target genes. In this example, 20±5 nucleotides located upstream of the poly (A) tail of the target gene by 109±8 nucleotides are used as sequences specific for 20 types of genes (i.e., ATP5B, GAPDH, GUSB, HMBS, HPRT1, RPL4, RPLP1, RPS18, RPL13A, RPS20, ALDOA, B2M, EEF1G, SDHA, TBP, VIM, RPLP0, RPLP2, RPLP27, and OAZ1), in order to standardize the PCR product size to approximately 200 nucleotides in the subsequent PCR amplification step. By standardizing the PCR product size, a complicated process of size fractionation and purification (electrophoresis, gel cleavage, and extraction and purification of PCR products) can be eliminated, and the PCR product can be directly used for parallel amplification from a single molecule (e.g., emulsion PCR). Subsequently, PCR amplification is carried out using universal sequences for amplification (forward/reverse), and PCR products 43 derived from multiple types of genes are prepared (FIG. 4(*f*)). Even if amplification bias occurs between genes or molecules in this step, amplification bias can be corrected with the use of a molecule recognition tag after acquisition of the data with the use of a next-generation sequencer. Thus, highly accurate quantification data can be obtained.

There are approximately $10^6$ mRNAs in a cell, and the nucleic acid trapping section for capturing such mRNAs is packed with $1.1 \times 10^5$ magnetic beads 12. Streptavidin is immobilized on a magnetic bead surface, and the 5' terminus of the DNA probe 31 may be modified with biotin, so that mRNAs are immobilized on the magnetic bead surface through streptavidin.

An embodiment in which 2nd cDNA is synthesized from cDNA generated on a bead surface (i.e., 1st cDNA) using several tens of types of gene-sequence-specific primers comprising universal sequences for PCR amplification added thereto, followed by PCR amplification, was described above. Alternatively, other amplification techniques, such as rolling circle amplification (RCA), NASBA, or LAMP, may be employed.

Subsequently, a method for preparing a device for nucleic acid extraction is described in detail. A nucleic acid trapping section packed with magnetic beads, a cell trapping section, and fluid channels connecting such sections were prepared using a substrate 6 made of polydimethylsiloxane (PDMS) by a semiconductor process. A cell trapping section comprises 10-µm through-holes arrayed at intervals of 125 µm. A substrate is a 13-mm square comprising $10^4$ cell trapping sections provided therein. The through-hole diameter is increased to 50 µm immediately below the cell trapping section, and this area is packed with magnetic beads. A porous array sheet (porous membrane) 35 was provided under the substrate 6 comprising through-holes arrayed thereon. The pore diameter of a porous array sheet is less than the diameter of a magnetic bead, which is 1 µm.

Thereafter, beads which have been separately introduced into an inkjet printer head and is comprising different sequences immobilized thereon are separately introduced into the nucleic acid trapping section 4 in amounts of 2 nl each.

The inner wall of each pore is made so as to be hydrophilic, such that it absorbs water, and it is capable of retaining beads in the nucleic acid trapping section. Various types of sheets may be used as a porous array sheet. For example, a monolith sheet of porous glass, a capillary plate prepared by forming a bundle of capillaries and slicing the bundle, a nylon membrane, or a gel thin membrane may be used. A porous array sheet obtained by anodic oxidation of alumina was used herein. While such a sheet can be produced via anodic oxidation, sheets with pore diameters of 20 nm to 200 nm and a diameter of 25 mm are commercially available. A 13-mm square was cut therefrom and used. A pore formed on the sheet serves as a fluid channel 5 that connects a nucleic acid trapping section to the lower reaction region.

The PDMS substrate and the porous array sheet were made to adhere to each other through plasma treatment.

In place of a PDMS substrate, a resin (e.g., polycarbonate, cyclic polyolefin, or polypropylene) substrate prepared via nanoimprinting or injection molding, a commercially available nylon mesh, or a track-etched membrane may be used. Such substrate and a porous array sheet may be made to adhere to each other via thermal adhesion.

Needless to say, such reaction layers may be integrated with each other in accordance with semiconductor processing.

Subsequently, a solution containing 1 µm diameter magnetic beads ($7 \times 10^9$ beads/ml) to which 5'-biotin-modified DNA probes have been immobilized is introduced into the nucleic acid trapping section 4 in amounts of 2 nl per region via the same technique as that used for inkjet printing. In this case, DNA probes having different cell recognition tag sequences (1,024 types) for relevant regions are discharged. A solution of magnetic beads is discharged through the fluid channel 5, and only beads remain. A DNA probe for capturing mRNA with different cell recognition tag sequences is immobilized to beads by mixing magnetic beads and DNA probe solutions in separate reaction tubes, mixing the resultant in Tris buffer containing 1.5 M NaCl (pH 7.4), and allowing the DNA probes to bind to the magnetic beads with rotation for 10 minutes.

Hereafter, the system of an apparatus for preparing the device for nucleic acid extraction and obtaining a gene expression profile using a next-generation (large-scale) sequencer is described with reference to FIG. 5. Up to about 1,000 cells were washed with 500 µl of 1× PBS without damaging the cells, a solution was removed so as to minimize the amount of PBS remained, and 50 µl of 1× PBS buffer cooled to 4° C. was added. Cells were introduced through the cell inlet 308, and buffer was discharged from the lower outlet 307, so as to align the cells in the form of an array in the cell trapping section. Excess cells were discharged from the upper outlet 306. Subsequently, lysis buffer was introduced through the upper inlet 305, PBS buffer was discharged through the fluid channels 306 and 307, and the content in the upper reaction region 7 was replaced with lysis buffer. The device for nucleic acid extraction is sandwiched by a transparent upper substrate 301 and a transparent lower substrate 302 from above and from underneath, respectively. Transparent electrodes (ITO) are formed inside these substrates via sputtering, and an electric field is applied to allow nucleic acids to migrate to the nucleic acid trapping section located immediately below the cells via electrophoresis. Electrodes are made transparent to facilitate the observation of cells under an optical microscope, and the ITO transparent electrodes used herein have permeability of 40% or higher in a wavelength range of 400 to 900 nm.

A lysis solution (495 ul, TaqMan MicroRNA Cell-to-CT Kit; Applied Biosystems Inc.) and DNase I (5 ul) were introduced through the inlet 305. After gelling of the solution was confirmed, temperature was raised to 20° C., the reaction was allowed to proceed for 8 minutes, 50 ul of a stopping solution (i.e., a solution that inactivates DNase) was added to the gel, the reaction was allowed to proceed for 5 minutes, and cooled to 4° C. Subsequently, 0.5 ml of 10 mM Tris buffer (pH 8.0) containing 0.03% polyethylene oxide (PEO) with a molecular weight of 600,000, 0.03% polyvinyl pyrrolidone (PVP) with a molecular weight of 1,000,000, and 0.1% Tween 20 was added. The distance between the upper electrode 301 and the lower electrode 302 was 2 mm, and the upper reaction region 7 and the lower reaction region 8 were completely filled with the Tris buffer. While the temperature of the solution was maintained at 4° C., the upper electrode 301 was designated as the cathode (GND), the lower electrode 302 was designated as the anode, a voltage of +5V was applied for 2 minutes using the power source 311, and negatively-charged mRNAs were electrophoresed from the inside of the cell toward the lower reaction region 8. Electrophoresis may be carried out with the application of a pulse with an on-level of 10 V, an off-level of 0 V, frequency of 100 kHz, and duty of 50% instead of the application of DC voltage. During this process, almost all mRNAs were captured (trapped) by oligo (dT) portions of the DNA probes immobilized on beads. However, some mRNAs were not captured because of their secondary structures and they migrated to the lower reaction region 8 located below the beads. In order to completely capture mRNAs with DNA probes, the temperature of the solution was raised to 70° C., maintained for 5 minutes, and cooled to 4° C. at −0.1° C./sec while reversing the polarity of the voltage applied to the lower electrode 302 every minute (a voltage of −5V was first applied for 1 minute, followed by alternate application of +5V and −5V for 1 minute ten times). Subsequently, the Tris buffer was introduced through the inlet 305 and discharged from the outlet 306, so as to exchange the solution in the upper reaction region 7, the temperature of the solution was raised to 35° C. to dissolve agarose gel, and unnecessary cellular tissues and agarose were removed by washing. In addition, 585 µl of 10 mM Tris buffer (pH: 8.0) containing 0.1% Tween 20, 40 µl of 10 mM dNTP, 225 µl of 5× RT buffer (SuperScript III, Invitrogen), 40 µl of 0.1M DTT, 40 µl of RNaseOUT (Invitrogen), and 40 µl of Superscript III (reverse transcriptase, Invitrogen) were mixed, solutions in the upper reaction region 7 and the lower reaction region 8 were discharged through the outlets 306 and 307, and the solution containing reverse transcriptase was immediately introduced through the inlet 305. Thereafter, the solution was warmed to 50° C., and maintained for 50 minutes so as to complete the reverse transcription reaction. Thus, 1st cDNA having a sequence complementary to mRNA was synthesized.

Libraries of cDNAs immobilized on the surfaces of many beads were obtained for each cell. Such libraries should be referred to as single-cell cDNA library arrays, which are fundamentally different from conventional cDNA libraries averaged among many cells.

With the use of the cDNA library arrays thus obtained, the expression level of each gene can be quantitatively assayed. Since 10,000 pores are present for a single cell, the average number of cDNAs per pore is 100. When the copy number of a single type of cDNA is not more than 10,000 per cell, the average number of cDNAs is not more than 1 per bead.

After the 1st cDNA strand was synthesized, it was allowed to stand at 85° C. for 1.5 minutes to deactivate the reverse transcriptase, and it was cooled to 4° C. Thereafter, 10 ml of 10 mM Tris buffer (pH: 8.0) containing RNase and 0.1% Tween 20 was introduced through the inlet 305 and discharged through the outlets 306 and 307. Thus, RNA was degraded, and the same amount of an alkaline denaturing agent was introduced in the same manner, so as to remove the substances remaining in the pores and degraded products, and the insides of the pores were then washed. Subsequently, 690 µl of sterile water, 100 µl of 10× Ex Taq buffer (TaKaRa Bio), 100 µl of 2.5 mM dNTP Mix, 100 µl of a mixture of 20 types of gene specific primers each added to 10 µM universal sequence for PCR amplification (reverse), and 10 µl of Ex Taq Hot start version (TaKaRa Bio) were mixed, a solution in the device was discharged through the outlets 306 and 307, and the solution containing reverse transcriptase was introduced through the inlet 305 immediately thereafter. A reaction of 95° C. for 3 minutes, 44° C. for 2 minutes, and 72° C. for 6 minutes was then performed to anneal the gene-specific sequence of the primers using the 1st cDNA strand as a template (FIG. 4(d)), and complementary strands were elongated to synthesize the 2nd cDNA strand (FIG. 4(e)).

Subsequently, 495 µl of sterile water, 100 µl of 10× High Fidelity PCR buffer (Invitrogen), 100 µl of 2.5 mM dNTP mix, 40 µl of 50 mM $MgSO_4$, 100 µl of 10 µM universal sequence for PCR amplification primer (forward), 100 µl of 10 µM universal sequence for PCR amplification primer (reverse), and 15 µl of Platinum Taq Polymerase High Fidelity (Invitrogen) were mixed, the solutions in the upper reaction region 7 and the lower reaction region 8 were discharged through the outlets 306 and 307, and, immediately thereafter, the solution was introduced through the inlet 305. Thereafter, the solution was maintained at 94° C. for 30 seconds, a 3-step process of 94° C. for 30 seconds, 55° C. for 30 seconds, and 68° C. for 30 seconds was repeated 40 times, and the reaction was maintained at 68° C. for 3 minutes at the end. The reaction was cooled to 4° C. and PCR amplification was then carried out (FIG. 4(f)). In order to actually perform such temperature cycle, a heat block (aluminum or copper alloy) 309 equipped with a heater and a temperature controller 310 may be added. Thus, target regions of 20 types of target genes are amplified, and the sizes of PCR products are substantially uniform; that is, the number of nucleotides is 200±8. The PCR-amplified product accumulated in the solution is collected. In order to remove free universal primer sequences for PCR amplification (forward/reverse) and remaining reagents such as an enzyme, the solution is purified using the PCR Purification Kit (QIAGEN). After the solution is subjected to emPCR amplification or bridge amplification, the solution is analyzed using next-generation sequencers (Solid/Ion Torrent (Life Technologies), High Seq (Illumina), and Roche 454).

Figure 6:
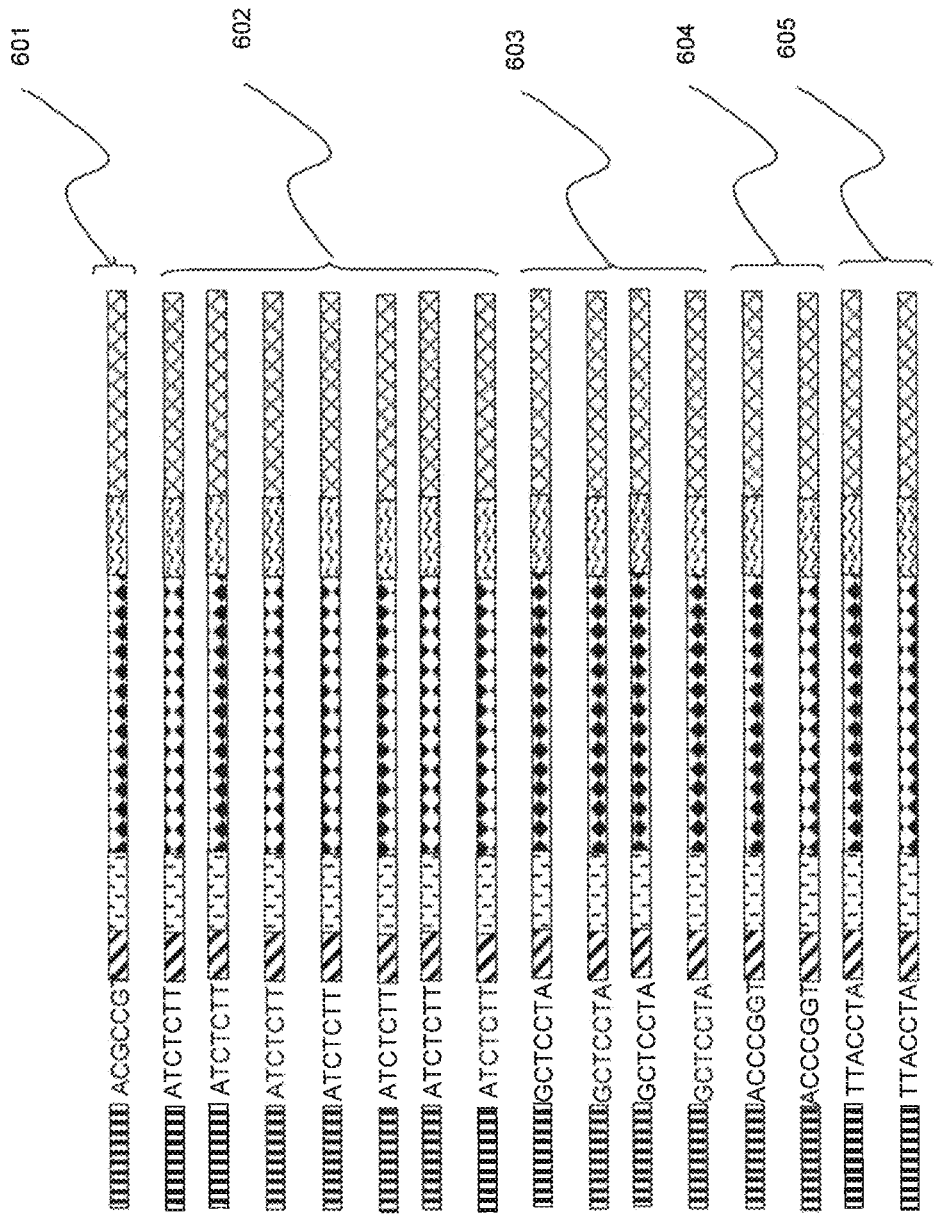
FIG. 6 schematically shows a nucleic acid used for the device for nucleic acid extraction according to an embodiment of the present invention.

Subsequently, a method for reducing the amplification bias using a molecule recognition tag is described. FIG. 6 schematically shows the conditions under which the information is attained via sequencing of the same sequence except for the molecule recognition region (i.e., FIG. 6 schematically shows a region correlated with the obtained sequencing information). In FIG. 6, 601, 602, 603, 604, and 605 indicate the same sequences including the molecule recognition tag sequences as random sequences, and 601, 602, 603, 604, and 605 indicate cases in which the number of reads is 1, 7, 4, 2, and 2, respectively. When the 2nd strand was synthesized in FIG. 4(e), the above sequences were each composed of a single molecule, the numbers of molecules increased as a result of subsequent PCR amplification, and the numbers of molecules became different from each other. Accordingly, the same reads in a molecule recognition tag may be regarded as indicating the same molecules, and such molecules are regarded as "single molecules." Thus, the bias in the number of molecules among sequences caused at the time of PCR amplification or adsorption of molecules to the inside of the porous array sheet when removing the solution after step of 2nd strand synthesis would be resolved.

As the information obtained herein, the apparent counts are 1, 7, 4, 2, and 2 (the identical sequence except for the molecule recognition tag). Molecules in a cell is collectively designated as "a count", and the total count is 5 (1, 7, 4, 2, and 2 each correspond to "a count"). That is, the number of molecules corresponding to a part of the sequence other than the molecule tag sequence is presumed to be 5 prior to amplification. In practice, the results of sequencing of a read sequence comprising a different sequence except for the molecule recognition tag can be obtained. In such a case, read sequences composed of the same sequences except for the molecule recognition tags may be analyzed, so that the sequences of interest can be analyzed. The original samples are deduced to contain mRNAs with a molecular number proportional to the results of analysis.

The sheets prepared herein can be repeatedly used. The expression levels of the genes of interest may be analyzed by preparing a mixture of a gene specific primer with a universal sequence primer for PCR amplification (reverse), in the same manner as described above, synthesizing the 2nd cDNA strand, amplifying the same via PCR and emPCR, and analyzing the resultant using a next-generation sequencer. With the repeated use of a cDNA library, specifically, gene expression distribution of the genes of interest can be assayed with high accuracy, according to need.

Example 2

In this example, a porous array sheet on which DNA probes are immobilized is used as the nucleic acid trapping section instead of a device for nucleic acid extraction comprising a bead-based nucleic acid trapping section, in order to construct a cDNA library of cells aligned in the form of an array while retaining the information concerning the cell origins of mRNAs contained in each cell. After the cDNA library is constructed, nucleic acid amplification is not carried out via PCR amplification, but nucleic acid amplification is carried out with the use of a T7 promoter.

Figure 8C:
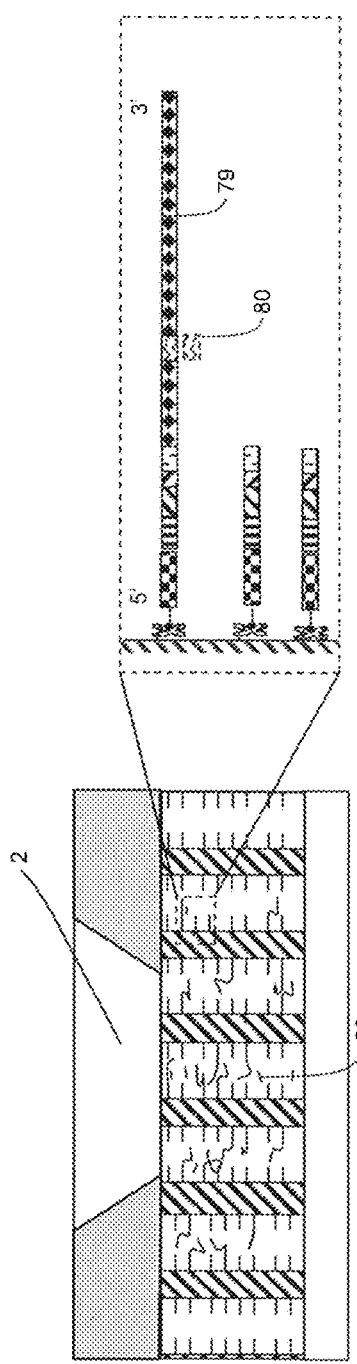
FIGS. 8C-8E schematically show a method of using the device for nucleic acid extraction according to an embodiment of the present invention.
Figure 8D:
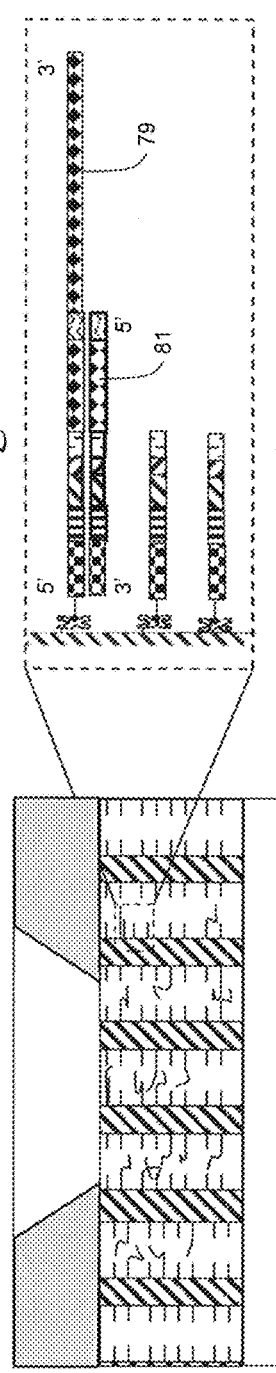
Figure 8E:
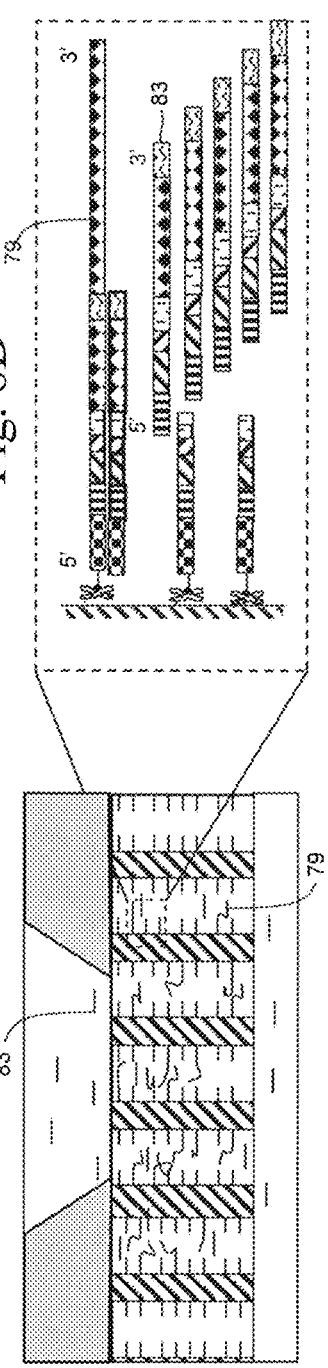
Figures 9F, 9G, 9H:
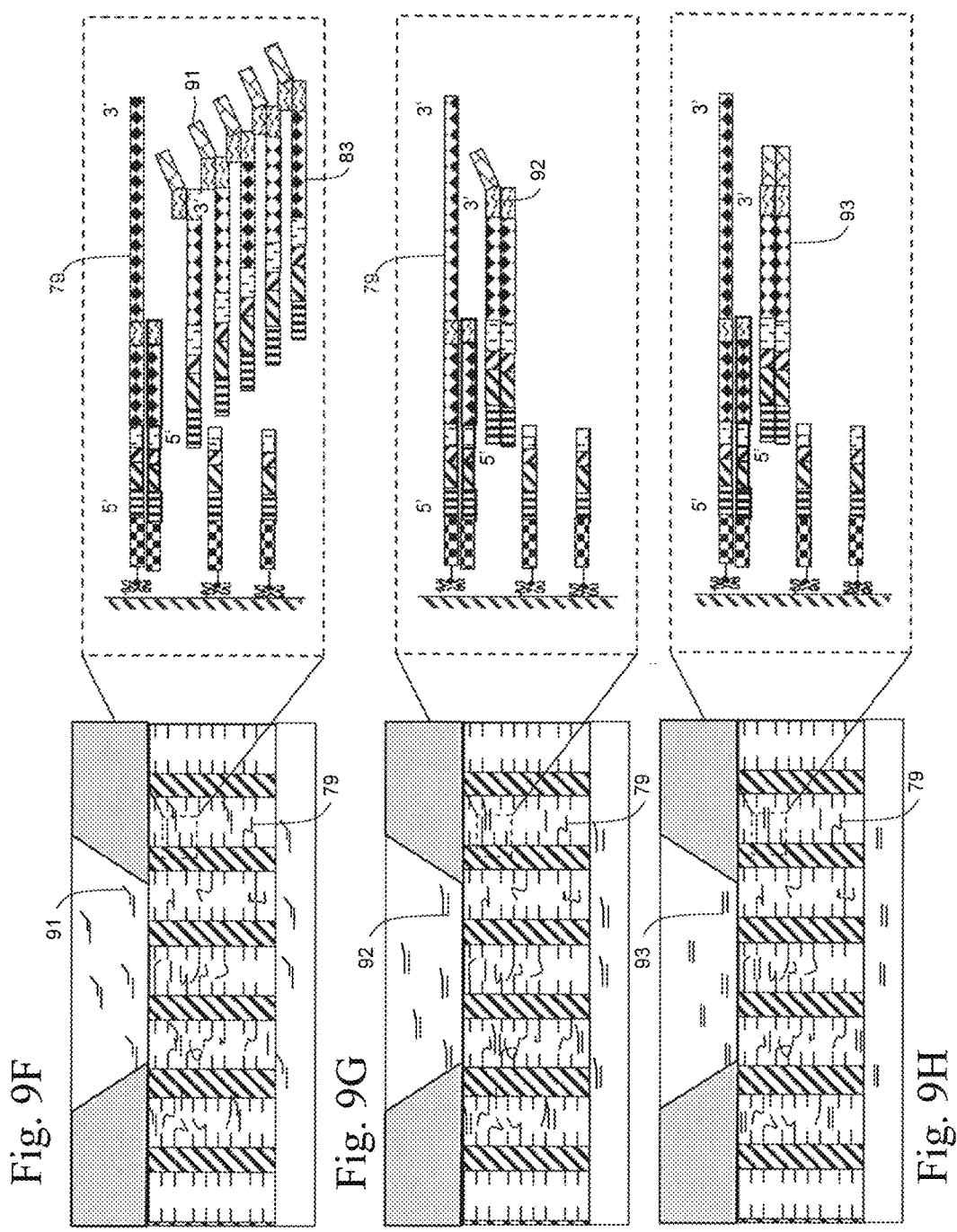
FIGS. 9F-9H schematically show a method of using the device for nucleic acid extraction according to an embodiment of the present invention.

FIGS. 7, 8, and 9 show the structure of the device for nucleic acid extraction used in this example and the method of extraction and treatment using the same.

FIG. 7(a) shows a cross section of a unit structure of the device for nucleic acid extraction. Cells 1 are captured (trapped) by the cell trapping section 2 by allowing a cell-containing buffer solution to flow through the device from the upper reaction region 7 toward the lower reaction region 8. The cell trapping section 2 is located inside the cell array device 6 made of PDMS. The diameter of the cell trapping section is 16 μm, which is somewhat greater than the cell diameter. Such diameter prevents the cell trapping section from capturing two or more cells. A nucleic acid trapping section (that is, the porous array sheet 71) is provided with many pores 72 that penetrate the sheet, and DNA probes are immobilized on the inner walls of the pores 72. The cell array device 6 made of PDMS for cell capture and the porous array sheet (porous membrane) 71 for nucleic acid trapping (capture) are the fundamental elements of the device for nucleic acid extraction. These two elements are directly superposed on top of each other, and such elements also serve as fluid channels connecting these two elements, in the same manner as in Example 1, cells are captured, a cell-containing buffer is substituted with a lysis buffer, and cells are disrupted while applying an electric field in a direction perpendicular to the device. Thus, mRNA in the disrupted cell is captured (trapped) by the DNA probe 73 on the inner wall of the pores 72 immediately below the cell trapping section via hybridization.

The DNA probe 73 immobilized within the cell array sheet comprises, from the 5' terminus, a T7 promoter sequence, a universal sequence for emPCR amplification (forward), a cell recognition tag sequence, a molecule recognition tag sequence, and an oligo (dT) sequence. By adding the T7 promoter sequence to the DNA probe, the target sequence can be amplified by the subsequent step of amplification of cRNA 83 via in vitro transcription (IVT) (FIG. 8(e)).

As described below, a DNA probe preferably comprises a promoter sequence of a transcription factor when cDNA is transcribed into cRNA with the aid of a transcription factor in the step of nucleic acid amplification. While a T7 promoter sequence is generally used, SP6, T3, and other promoter sequences can be used. Nucleic acid amplification is carried out with the aid of activity of T7 RNA polymerase.

In this example, the T7 promoter sequence is used, this sequence is recognized by the T7 RNA polymerase, and transcription (amplification of cRNA 83) is initiated from the downstream sequence thereof.

Nucleic acid amplification involving the use of a promoter sequence of a transcription factor can be carried out under isothermal conditions. Accordingly, it is not necessary to perform a temperature cycle with the use of a temperature controller. In addition, the possibility of probe DNA immobilized on the devise surface becoming detached at high temperature can be reduced.

By adding a universal sequence for PCR amplification, also, it can be used as a universal primer in the subsequent process of emPCR amplification. In addition, addition of a cell recognition tag to a DNA probe comprising, for example, 5 nucleotides enables recognition of $4^5$=1,024 single cells, as with the case of Example 1. Further, addition of a molecule recognition tag sequence comprising, for example, 7 nucleotides into a DNA probe enables recognition of $4^7$=1.6×$10^4$ molecules. Accordingly, the molecule origin of numerous decoded data obtained with the use of a next-generation sequencer can be identified, as with the case of Example 1. Specifically, an amplification bias among genes generated in the amplification process, such as IVT or emPCR, can be corrected, and the amount of mRNA existing in the sample at the beginning can be quantified with high accuracy. An oligo (dT) sequence located in a region closest to the 3' terminus hybridizes to the poly (A) tail added to the 3' side of mRNA to capture (trap) mRNA (FIG. 7(a)).

Subsequently, a method for preparing a porous array sheet constituting the nucleic acid trapping section is described.

A porous array sheet prepared by anodic oxidation is commercially available, and an embodiment in which a 13-mm square porous array sheet 71 with a pore diameter of 200 nm and a thickness of 60 μm (cut from a sheet with a diameter of 25 mm) is used is described herein. Pores 72 provided on the porous array sheet 71 penetrate the porous array sheet 71 in its thickness direction, and pores are completely independent of each other. The pores 72 also serve as the fluid channel 5. Because of hydrophilic properties of the surface, the amount of proteins adsorbed to the surface is very low, and the enzyme reaction proceeds efficiently. At the outset, the surface of the porous array sheet 71 is subjected to slime coupling or another form of treatment so as to immobilize the DNA probe 73 on the surface of the pores. Since the DNA probes 73 are immobilized on the surface at a density of one every 30 to 100 $nm^2$ on average, 4 to 10×$10^6$ DNA probes are immobilized to a pore. Subsequently, a surface is coated with a surface coating agent so as to prevent surface adsorption. The surface coating may be carried out simultaneously with probe immobilization. At such DNA probe density, mRNAs that pass through this space can be substantially completely captured (trapped) by DNA probes with an efficiency of substantially 100%.

Subsequently, a method for immobilizing DNA probes inside the pores is described in detail. It is necessary that the surface of the pore inside the porous array sheet be capable of comprising DNA probes immobilized at high density thereon and that the surface not adsorb nucleic acids, such as mRNA and primers for PCR amplification, or proteins, such as reverse transcriptase and polymerase. In this example, a silane coupling agent used for immobilizing DNA probes and a silane-coupled MPC polymer used for preventing adsorption were simultaneously immobilized at an adequate ratio on the pore surface via covalent binding, DNAs were immobilized at high density, and adsorption of nucleic acids and proteins was stably inhibited. In practice, a porous array sheet made of alumina was immersed in an ethanol solution for 3 minutes, treated with UVO3 for 5 minutes, and then washed with ultrapure water three times. The resultant was then immersed in a 80% ethanol solution containing a silane-coupled MPC polymer with an average molecular weight of 9,700 (polymerization degree: 40); that is, 3 mg/ml of $MPC_{0.8}$-$MPTMSi_{0.2}$ (MPC: 2-methacryloyloxyethyl phosphorylcholine; MPTMSi; 3-methacryloxypropyl trimethoxysilane) (e.g., Biomaterials 2009, 30: 4930-4938; and Lab Chip 2007, 7: 199-206), 0.3 mg/ml of a silane coupling agent (GTMSi: 3-glycidoxypropyltrimethoxysilane; Shin-Etsu Chemical Co., Ltd.), and 0.02% acetic acid as an acid catalyst for 2 hours. The product was washed with ethanol, dried in the nitrogen atmosphere, and then heated in an oven at 120° C. for 30 minutes. In order to immobilize DNA, 1 μM 5'-amino-modified DNA probes, 7.5% glycerol, and a 0.05 M borate buffer (pH 8.5) containing 0.15 M NaCl was then discharged onto the porous array sheet using the same technique as that used for inkjet printing in such a manner that DNA probes containing different cell recognition tag sequences (1,024 types) would be discharged in an amount of 100 pl for every 25-μm-square region. Thereafter, the reaction was allowed to proceed in a moisture chamber at 25° C. for 2 hours. At the end, an unreacted glycide group was blocked, and excessive DNA probes were removed by washing with a sufficient amount of borate buffer (pH 8.5) containing 10 mM Lys, 0.01% SDS, and 0.15 M NaCl for 5 minutes. After the wash solution was removed, excessive DNA probes were removed by washing with a 30 mM sodium citrate buffer (2×SSC, pH 7.0) containing 0.01% SDS and 0.3 M NaCl at 60° C. Thus, DNA probe immobilization and surface treatment were completed.

Subsequently, reaction steps are described sequentially. As shown in FIG. 7(a), mRNA 74 is captured by an 18-bp poly (T) sequence, which is complementary to the poly (A) sequence at the 3' terminus of mRNA in the same manner as in the previous example. The 1st cDNA strand 79 is then synthesized to construct a cDNA library (FIG. 7(b)). Subsequently, the primer 80 specific for a plurality of types (~100 types) of target gene sequences corresponding to the gene to be quantified is allowed to anneal to the 1st cDNA strand 79 (FIG. 8(c)), and the 2nd cDNA strand 81 is synthesized via complementary strand extension (FIG. 8(d)). Specifically, the 2nd cDNA strand is synthesized under multiplex conditions. Thus, double-stranded cDNAs of the plurality of target genes are synthesized, and such double-stranded cDNAs each comprise, at both terminuses, universal sequences for amplification (forward/reverse), cell recognition tags, molecule recognition tags, and gene-specific sequences. In this example, regions comprising 20±5 nucleotides located 109±8 nucleotides upstream f the poly (A) tail of the target gene were used as 20 types of gene-specific sequences (i.e., ATP5B, GAPDH, GUSB, HMBS, HPRT1, RPL4, RPLP1, RPS18, RPL13A, RPS20, ALDOA, B2M, EEF1G, SDHA, TBP, VIM, RPLP0, RPLP2, RPLP27, and OAZ1) in order to standardize the amplification product size to approximately 200 nucleotides in the subsequent step of amplification via IVT. By standardizing the PCR product size, a complicated process of size fractionation and purification (electrophoresis, gel cleavage, and extraction and purification of PCR product) can be eliminated, and such technique can be directly applied to parallel amplification from a single molecule (e.g., emulsion PCR). Subsequently, T7 RNA polymerase is introduced into pores to synthesize cRNA 83 (FIG. 8(e)). Thus, approximately 1,000 copies of cRNAs are synthesized. In order to synthesize double-stranded DNA for emPCR, in addition, the amplified cRNA is used as a template to hybridize the primer 91 specific for a plurality of types (~100 types) of target gene sequences to which the universal sequence for PCR amplification (reverse) had been added (FIG. 9(f)), so as to synthesize cDNA (FIG. 9(g)). In addition, cRNA is degraded with the use of an enzyme in the same manner as in the previous example, the 2nd strand 92 is synthesized using the universal forward primer, and double-stranded DNA 93 for emPCR is then synthesized (FIG. 9(h)). The lengths of the amplification products obtained above are uniform, and such amplification products can be applied to emPCR or a next-generation sequencer without further treatment. Even if an amplification bias is generated between genes or molecules in this process, the amplification bias can be corrected with the use of a molecule recognition tag after the data is attained with the use of a next-generation sequencer. Accordingly, highly accurate quantification data can be obtained, as in the case of the previous example.

Subsequently, a process carried out with the use of the apparatus shown in FIG. 10 having the unit structure of the device for nucleic acid extraction shown in FIG. 7 is specifically described. FIG. 10(b) is a cross section taken along A-A' of FIG. 10(a) and FIG. 10(c) is a cross section corresponding to the cross section taken along B-B' of FIG. 10(a). The process of introducing cells 1 through the cell inlet 308, allowing the cell trapping section 2 to capture the cells, and synthesizing the 1st cDNA strand is carried out in the same manner as in Example 1. After the 1st cDNA strand was synthesized, it was allowed to stand at 85° C. for 1.5 minutes to inactivate a reverse transcriptase, and the temperature was reduced to 4° C. Thereafter, RNase and 10 ml of 10 mM Tris buffer (pH: 8.0) containing 0.1% Tween 20 were introduced through the inlet 305 and discharged through the outlets 306 and 307. Thus, RNA was degraded, the equivalent amount of alkaline denaturing agent was allowed to flow though in the same manner, so as to remove the substances remaining in the pores and degraded products, and the insides of the pores were then washed. Subsequently, 690 μl of sterile water, 100 μl of 10× Ex Taq buffer (TaKaRa Bio), 100 μl of 2.5 mM dNTP mix, 100 μl of a mixture of 20 types of gene-specific primers added to universal sequences (10 μM each) for PCR amplification (reverse), and 10 μl of Ex Taq Hot start version (TaKaRa Bio) were mixed. The solutions in the upper reaction region 7 and the lower reaction region 8 were discharged through the outlets 306 and 307, and, immediately thereafter, the solution containing a reverse transcriptase was introduced thereinto through the inlet 305. Thereafter, a reaction was carried out at 95° C. for 3 minutes, 44° C. for 2 minutes, and 72° C. for 6 minutes, the gene-specific sequence of the primer was allowed to anneal to the 1st cDNA strand as a template, and the 2nd cDNA strand was synthesized via complementary strand extension.

Subsequently, 10 ml of 10 mM Tris buffer (pH: 8.0) containing 0.1% Tween 20 was introduced through the inlet 305 and discharged through the outlets 306 and 307, so as to remove the substances remaining in the pores and degraded products, and the insides of the pores were then washed. In addition, 340 μl of sterile water, 100 μl of AmpliScribe 10× Reaction buffer (EPICENTRE), 90 μl of 100 mM dATP, 90 μl of 100 mM dCTP, 90 μl of 100 mM dGTP, 90 μl of 100 mM dUTP, 90 μl of 100 mM DTT, and 100 μl of AmpliScribe T7 Enzyme Solution (EPICENTRE) were mixed, the solutions in the upper reaction region 7 and the lower reaction region 8 were discharged through the outlets 306 and 307, and, immediately thereafter, the solution containing a reverse transcriptase was introduced through the inlet 305. Thereafter, the temperature of the solution was raised to 37° C. and maintained for 180 minutes to complete the reverse transcription, and cRNA amplification was carried out. Thus, target regions of 20 types of target genes were amplified, and the sizes of cRNA amplification products were substantially uniform; that is, the number of nucleotides was 200±8. The cRNA amplification products accumulated inside the membrane pores and accumulated in the solution outside thereof were collected. The solution was purified with the use of the PCR Purification Kit (QIAGEN) in order to remove remaining reagents such as an enzyme therefrom, and the resultant was suspended in 50 µl of sterile water. To the solution, 10 µl of 10 mM dNTP mix and 30 µl of 50 ng/µl random primer were added, the mixture was heated to 94° C. for 10 seconds, cooled to 30° C. at 0.2° C./sec, the resultant was heated at 30° C. for 5 minutes, and further cooled to 4° C. Thereafter, 20 µl of 5× RT buffer (Invitrogen), 5 µl of 0.1 M DTT, 5 µl of RNase OUT, and 5 µl of SuperScript III were mixed, the mixture was heated at 30° C. for 5 minutes, and the temperature was raised to 40° C. at 0.2° C./sec. The solution was purified with the use of the PCR Purification Kit (QIAGEN) in order to remove remaining reagents (such as an enzyme) therefrom, the resultant was subjected to emPCR amplification, and the amplified product was then analyzed using next-generation sequencers (Life Technologies, Illumina, and Roche).

Example 3

The device for nucleic acid extraction that implements single-cell gene analysis is capable of identifying individual properties/conditions of cells. In contrast, non-invasive microscopic observation is capable of assaying configurations and chemical compositions of cells while the cells remain alive. However, it has been very difficult to identify cellular conditions based only on the information obtained by microscopic imaging because individual properties/conditions of cells are diverse and unstable. In this example, the constitutions of the device and the apparatus that implements identification of individual properties of cells via single-cell gene analysis in combination with non-invasive imaging are described. When microscopic observation is performed while capturing cells with the use of the device as shown in FIG. 3(a) or FIG. 7(a), in general, the refractive index of a transparent material constituting beads or porous sheets is different from that of a solution. Accordingly, an excited light and an illuminated light scatter, disadvantageously leading to lowered resolution and increased background light. This example demonstrates an embodiment in which the device for nucleic acid extraction typified by the structure shown in FIG. 2 is used in combination with an optical microscope.

FIG. 11 shows the device for nucleic acid extraction and the apparatus used in this example. FIG. 11(b) is a cross section taken along A-A' of FIG. 11(a) and FIG. 11(c) is a cross section corresponding to the cross section taken along B-B of FIG. 11(a). In this example, the configuration of the substrate 6 made of PDMS was modified in such a manner that a ring-shaped nucleic acid trapping section was provided in the vicinity of the cells instead of a region immediately below the cells and packed with magnetic beads 12. With the application of an electric field in a direction perpendicular to the substrate plane, nucleic acids such as mRNAs are electrophoresed to beads packed in a ring shape and captured by DNA probes on the bead surface. The process described below is the same as that described in Example 1. The diameter of the cell trapping section made of PDMS was adjusted to 16 µm, and the microscope window 1101 located immediately below the cell trapping section was adjusted to have a diameter of 25 µm and a height of 15 µm. Also, the porous array sheet 35 is protected via resist masking at the time of anodic oxidation, so that pores would not be formed in a region immediately below the cell trapping section. Without patterning anodic oxidation, the thickness of the microscope window 1101 may be adjusted to be larger than the focal depth in a direction perpendicular to the device plane of the optic microscope. Thus, the influence imposed by scattering caused by the porous array sheet can be reduced.

As shown in FIG. 12, the nucleic acid trapping section can be provided next to the cells instead of in the vicinity of the cells. FIG. 12(b) is a cross section taken along A-A' of FIG. 12(a) and FIG. 12(c) is a cross section corresponding to the cross section taken along B-B' of FIG. 12(a). In this example, "1201" indicates a nucleic acid trapping section. In this case, also, DNA probes are immobilized on beads to capture mRNAs. Other device structures and methods for sample preparation are e same as those described in Example 1.

While regions packed with beads are designated as nucleic acid trapping sections in FIGS. 11 and 12, the region in which pores are provided is limited, as in the case of Example 2 in which the porous array sheet is designated as the nucleic acid trapping section. This enables production of a device with the same constitution as those shown in FIGS. 11 and 12 without the use of beads.

Before conducting thorough gene expression analysis by disrupting cells with the use of such device for nucleic acid extraction, genes or proteins are subjected to quantification or high-resolution Raman imaging via observation of living cells or fluorescent staining, and the image data can be correlated with the gene expression analysis data. The constitution of a system for implementing such correlation is described below.

Figure 13:
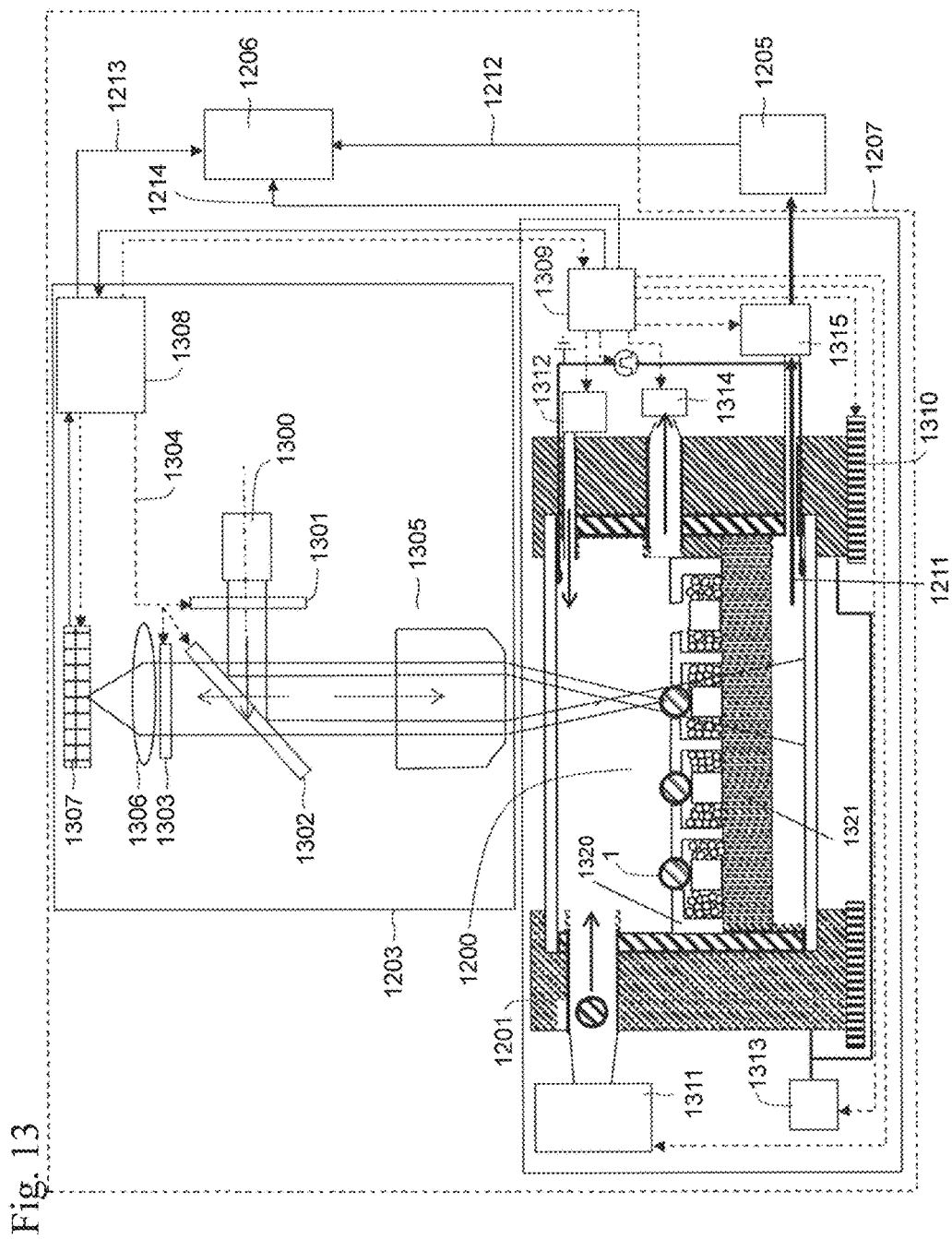
FIG. 13 schematically shows the apparatus for nucleic acid treatment according to an embodiment of the present invention.

FIG. 13 shows a minimal constitution of a system for conducting thorough assays of cellular kinetics of cell samples provided on a planar device (e.g., the cell array 1320, the porous array sheet 1321), so as to construct a device for nucleic acid extraction, by correlating the results of optical microscopic assay and the results of gene expression analysis conducted with the use of the device for each cell "1200" represents a device for nucleic acid extraction and a cell sample provided on the device. "1201" represents a flow system for conducting mRNA extraction from cells and nucleic acid amplification typified by FIG. 11. By treating cell-derived mRNA in this flow system, amplification products in amounts necessary for conducting sequencing with the use of a next-generation (large-scale) DNA sequencer 1205 of a given length and comprising tag sequences with the information from before nucleic acid treatment recorded at the terminus are obtained. An arrow 1211 indicates migration of the amplification product. The positions of the cells on the device are identified in advance and the cells are observed under the optical microscope 1203 in such state. A thin arrow indicates migration of information. The optical microscope 1203 may be, for example, a phase contrast microscope, a differential interference microscope, a fluorescence microscope, a confocal laser scanning fluorescence microscope, a Raman microscope, a non-linear Raman microscope (a CARS, SRS, or RIKE microscope), or an IR microscope. The amount of genetic information that can be obtained with the use of such optical microscopes is small. Basically, cells can be assayed while they are alive, time-dependent changes of the cells can be assayed, and cellular responses to stimulation can be assayed in real time. With the use of a device conserving the positional information on the device, thorough information regarding gene expression can be correlated with information including that on time-dependent changes obtained via microscopic observation. To this end, a system is required to be provided with the information system 1206 that integrates the sequence information 1212 obtained with the use of a next-generation (large-scale) DNA sequencer, the image information 1213 obtained with the use of an optical microscope, and the positional information 1214 correlated with the tag sequence. According to the present invention, the minimal constitution of the system that integrates the cell assay information described above is a system 1207 provided in a region other than the next-generation (large-scale) DNA sequencer 1205, and such system is capable of inputting the information into the DNA sequencer and a sample (i.e., a nucleic acid amplification product).

FIG. 13 shows an example of a system constitution when a fluorescence microscope is used as an optical microscope, "1203" represents a fluorescence microscope. In cells 1, GFP is expressed in a protein to be assayed (e.g., p53) or a fluorophore is introduced into a particular protein via immunostaining. The information concerning the protein expression level in each cell thus obtained can be correlated with the information concerning gene expression obtained by disrupting the cells, processing the information in the device for nucleic acid extraction, and conducting quantification via DNA sequencing for each cell. In this case, a nucleic acid is stained by DAPI to identify the cell, and a cell nucleus is identified, thus enabling identification of the position of the cell under the fluorescence microscope. Since the protein level is assayed on the basis of GFP expression, time-dependent changes can be observed, although only a few types of proteins that can be simultaneously assayed. In contrast, approximately 100 genes can be simultaneously subjected to gene expression analysis via sequencing, and as many as 1,000 types of genes can be simultaneously assayed with the use of probes. Thus, thorough information concerning gene expression control in cells can be obtained for each cell. This technique, however, does not make it possible to observe time-dependent changes. If information concerning the correlation between protein expression and gene expression is obtained in advance by implementing the techniques described above in combination, information concerning gene expression control can be deduced based only on the information concerning protein expression. Correlation of the fluorescence microscopic data and the gene expression data and deduction of the information concerning gene expression control are implemented via the information system 1206.

Subsequently, the constitution of the fluorescence microscope 1203 is described in detail. "1300" represents a light source, which is a mercury lamp herein, "1301" represents an excitation filter hat determines the excitation wavelength, "1302" represents a dichroic mirror, and "1303" represents an emission filter that selects the light-receiving wavelength. When a plurality of types of fluorophore are introduced into a cell and assayed simultaneously, 1301, 1302, and 1303 are selected by the controller 1304, and lights from particular fluorophores are selectively assayed. Fluorescence imaging of cells is carried out with the use of an objective lens 1305, an imaging lens 1306, and a CCD camera 1307. A control computer 1308 controls these elements and acquires the image data.

A control system for the flow system 1201 is then described. "1309" represents a control computer for the flow system, which controls the XY stage 1310 and transfers the microscopic images. On the control computer, positional coordinates on the porous array sheet can be correlated with the microscopic positional coordinates determined based on the cell recognition tag sequence information and the XY stage positional coordinates. The control computer 1309 adequately controls a cell introduction control unit 1311 that controls introduction of cells into the flow cell system, a reagent control unit 1312 that controls introduction of a differentiation inducer that alters cellular conditions, an agent, responses of which to the cells are to be inspected, a lysate for cell disruption, and a reagent used for sample treatment, a temperature and $CO_2$ concentration control unit 1313 that controls cell culture conditions and the temperature cycle of PCR, an upper reagent discharge unit 1314 that discharges unnecessary reagents, cells, or media, and a lower reagent discharge unit 1315 that discharges the nucleic acid amplification products. The final nucleic acid amplification product is transferred to the next-generation (large-scale) DNA sequencing system 1205 and subjected to sequence analysis. In this case, emPCR or bridge amplification is implemented for sequencing in this system. The positional image information and the cell recognition tag sequence information checked via the control computer are transferred to the integrated information system 1206, and the protein expression level obtained by fluorescence imaging and the gene expression levels are correlated with each other. In addition, time-dependent changes in information concerning gene expression analysis are deduced using the same system. Thus, the dynamics of a gene expression network can be assayed.

While the fluorescence microscope described above may be used for intracellular assays, it may be also used to introduce a substance secreted from a cell, such as a captured cytokine, into a porous array sheet to immunofluorescently stain with an antibody and to assay the amount thereof. Similarly, such microscope may be used for gene expression analysis after cells have been disrupted.

Figure 14:
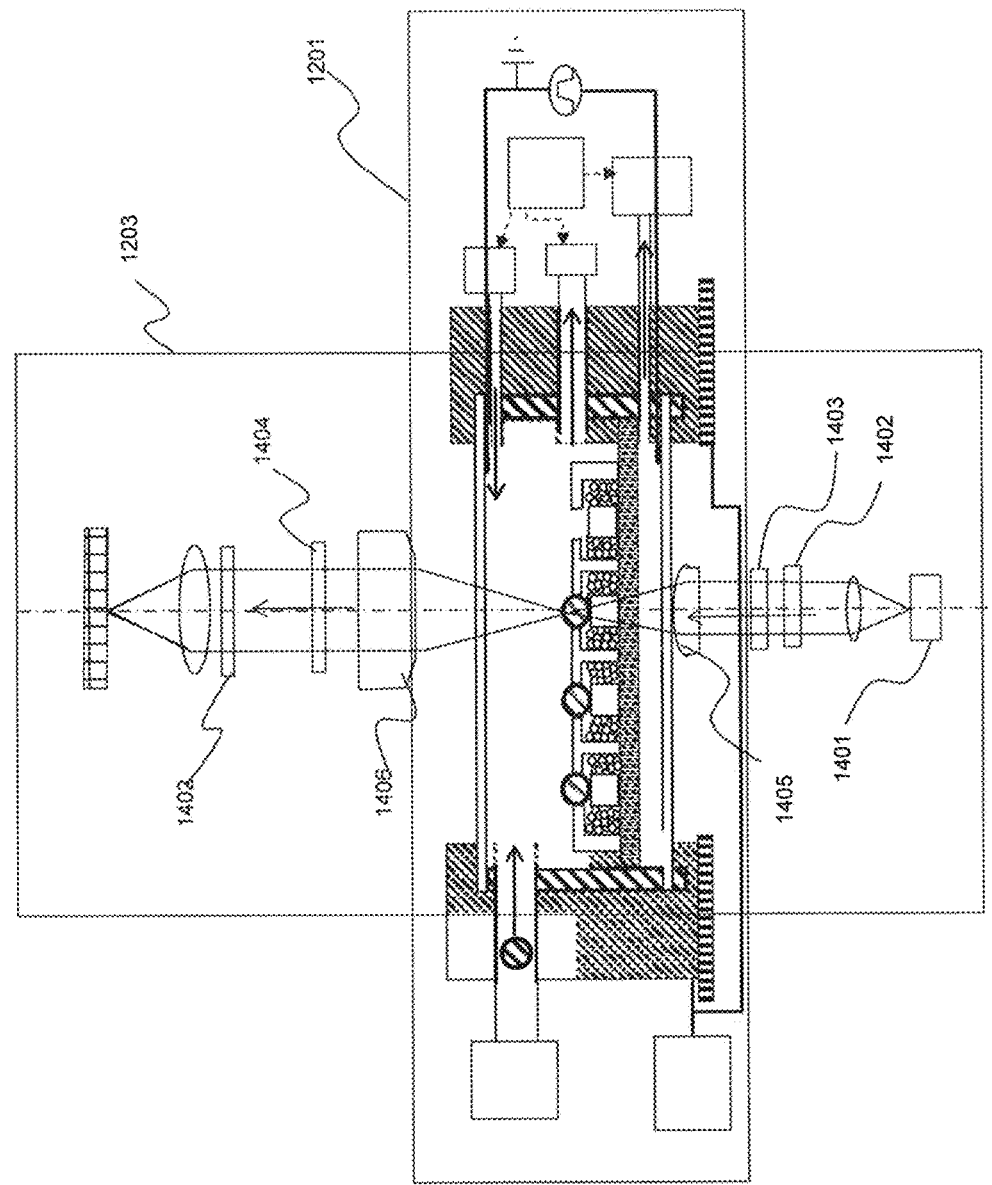
FIG. 14 schematically shows the apparatus for nucleic acid treatment according to an embodiment of the present invention.

FIG. 14 shows an example in which a differential interference microscope is used instead of a fluorescence microscope. According to differential interference microscopy, the cellular configurations are merely assayed without the use of a fluorescence reagent. The influence of such assay technique on cells is minimal when cells must be re-introduced into the body, such as in the case of regenerative medicine. When changes in cellular configurations identified via the image can be correlated with changes in gene expression, such assay system would impose the least damage on cells, and cells can be precisely classified.

"1401" represents a light source, which is a halogen lamp herein. "1402" represents a polarizer, and "1403" and "1404" represent a Wollaston filter and a Wollaston prism, respectively. "1405" represents a condenser lens, and "1406" represents an objective lens.

Figure 15:
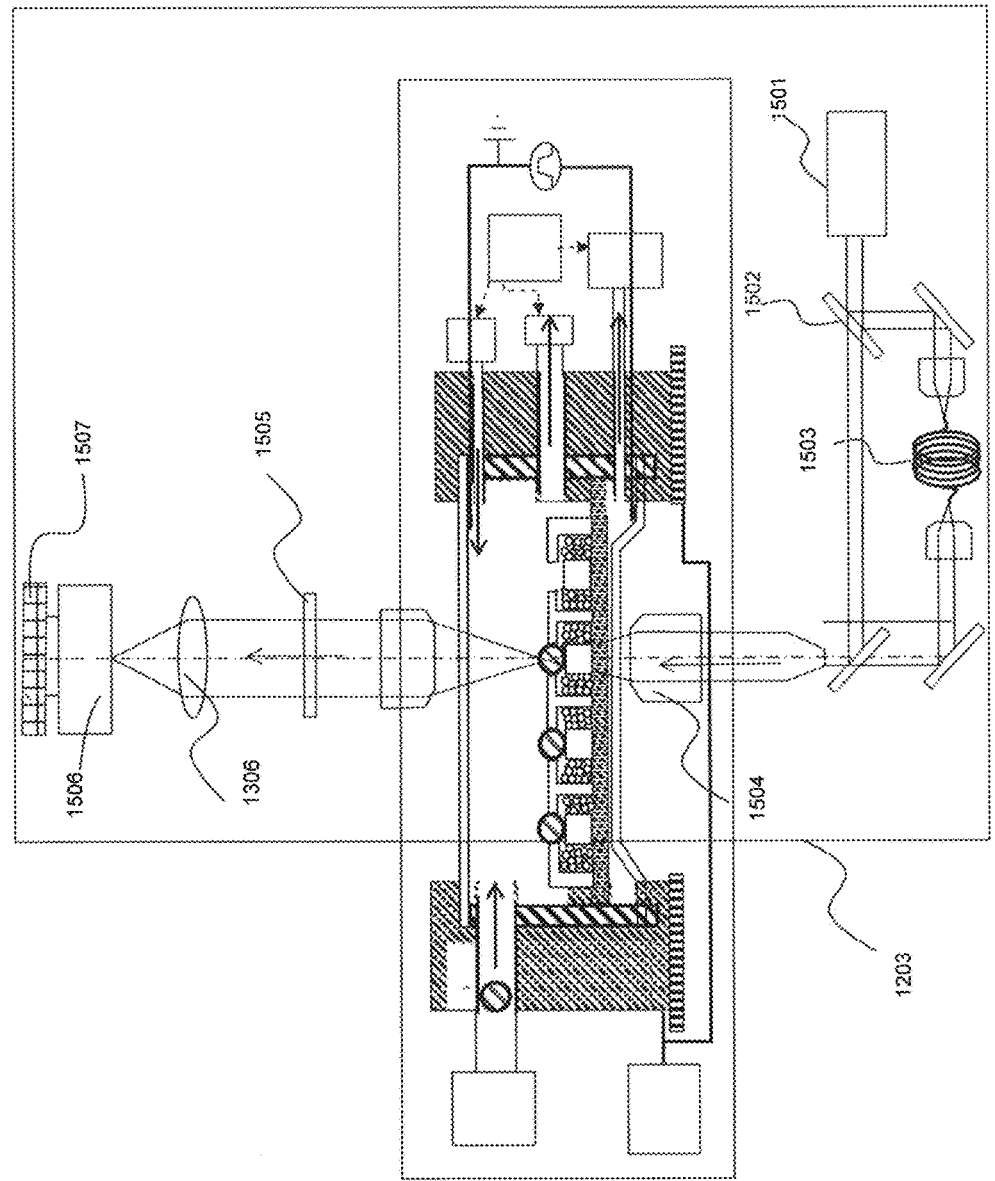
FIG. 15 schematically shows the apparatus for nucleic acid treatment according to an embodiment of the present invention.

FIG. 15 shows an example in which a CARS microscope is used as an optical microscope. As with Raman microscopes and IR microscopes, spectra in accordance with the chemical species in the laser-excited area can be attained using CARS microscopes. Thus, the amount of information concerning cellular conditions can be larger than that attained with the use of differential interference microscopes. During a non-linear process, signals can be attained to a sufficient extent with CARS at a higher signal intensity and a relatively lower laser excitation intensity, compared with Raman signals. Thus, damages imposed on cells can be small. By correlating such CARS image and the gene expression analysis data, cellular conditions can be determined with higher accuracy.

"1501" represents a light source, which is a pulse laser (microchip laser) herein. The light source is split in two with the aid of the beam splitter 1502, and one of the split beams is introduced into the nonlinear fiber (a photonic crystal fiber) 1503 to generate a Stoke's beam. The other beam is used as a pump light or probe light, and the beams are collected in the sample (cell) with the use of the immersion objective lens 1504 to generate an anti-Stoke's beam. The anti-Stoke's light is selectively allowed to penetrate and pass through the high-pass filter 1505 and the spectrometer 1506, making it possible to obtain coherent anti-Stokes Raman spectra using the CCD camera 1507 for the spectrometer.

Example 4

Figure 16:
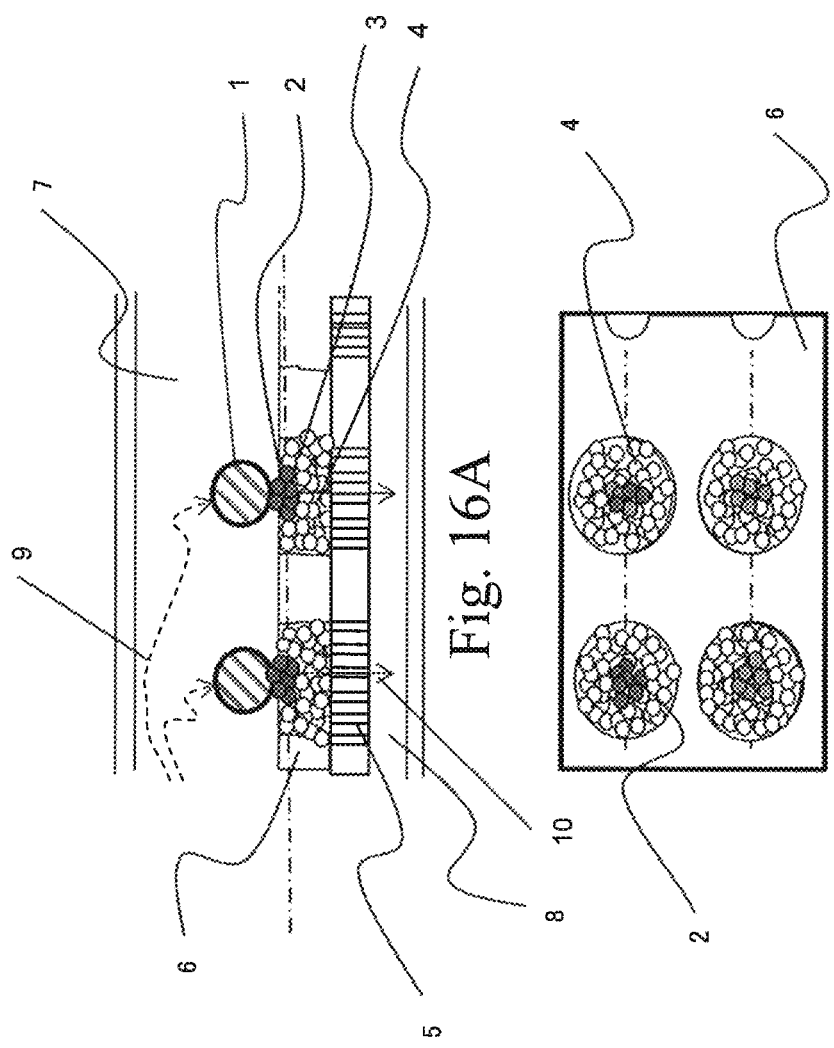
FIGS. 16A and 16B schematically show the device for nucleic acid extraction according to an embodiment of the present invention.

In this example, the cell trapping section is not provided as an aperture in a size equivalent to a cell, but it is composed of a region on which a substance that chemically captures a cell surface (that is, a substance that chemically binds to a substance on a cell surface) is immobilized. FIG. 16 shows an example in which a cell trapping section is modified in accordance with Example 1 (FIG. 1). Beads comprising proteins such as antibodies that bind to the cell surface immobilized thereon are provided in some beads used for nucleic acid trapping (capture). Antibodies on the beads can be provided with functions of capturing a particular type of cell. For example, a group of antibodies referred to as the cluster of differentiation (CD) antibodies correspond to types of membrane proteins of cells that are mainly leukocytes. The antibodies are biotinylated and immobilized with the aid of streptoavidin on the beads, the heads are introduced into the cell trapping section 2 shown in FIG. 16 via inkjet printing, and cells having antigens of particular CD types can then be captured. CD antibodies may not be necessarily immobilized directly on beads, and they may be immobilized on beads with the aid of biotin-modified secondary antibodies. Also, antibodies other than the CD antibodies may be immobilized on beads, or molecules that bind to receptors on the cells may be immobilized. An example of such a molecule is fibronectin. Fibronectin is known to bind to integrin on cells. By immobilizing fibronectin on beads, adhesive cells can be captured.

Examples of other substances that chemically bind to substances on the cell surface include extracellular matrices, such as collagen, laminin, and elastin.

Figure 17:
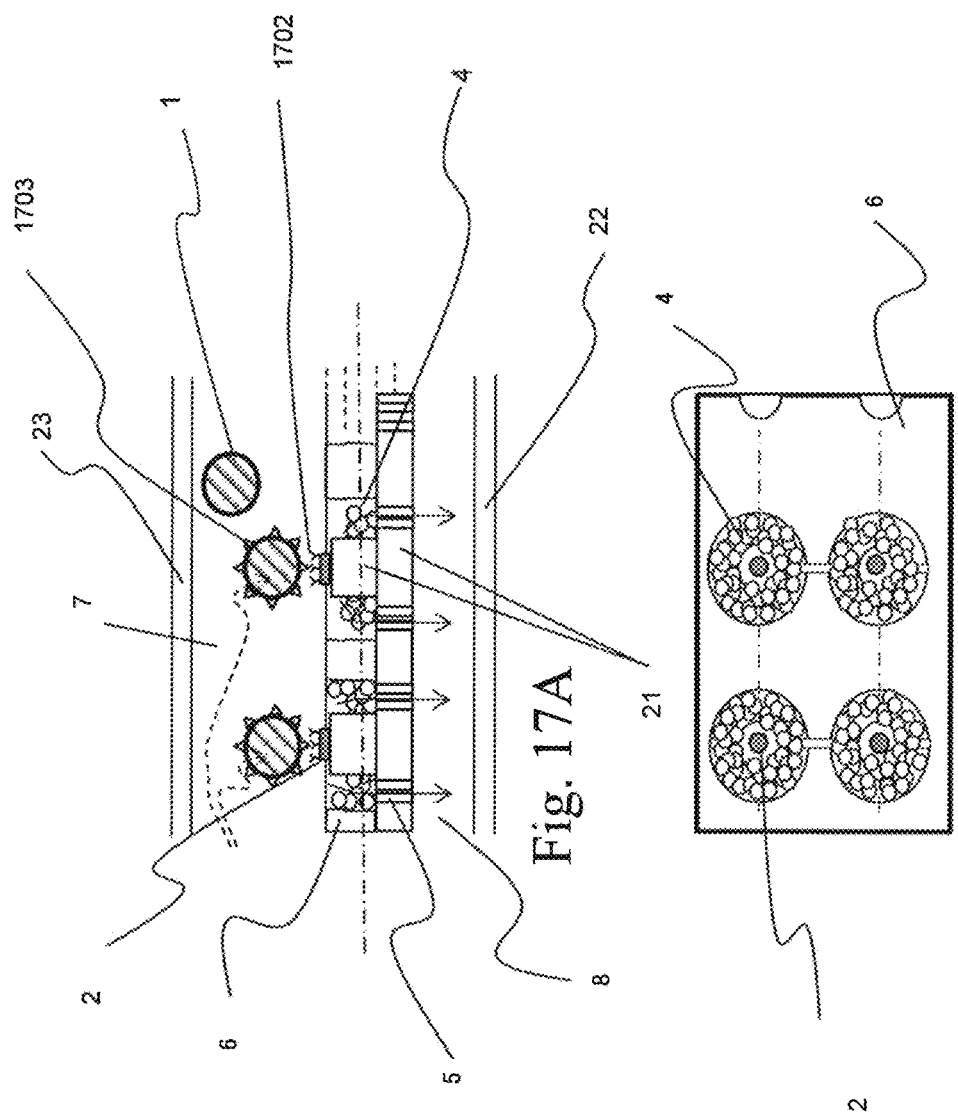
FIGS. 17A and 17B schematically show the device for nucleic acid extraction according to an embodiment of the present invention.

Subsequently, an example in which cell capture is chemically carried out with the use of a device structure comparable to Example 3 (FIG. 2) is described. In this example, a substance used for cell capture is immobilized in a part of a transparent region of the device for nucleic acid extraction. A substance used for cell capture may be an antibody as described above, or it may be a different substance. FIG. 17 shows an example of a constitution of the device for nucleic acid extraction. The antibody 1702 for cell capture is immobilized on the cell trapping section 2 via immobilization of the biotinylated antibody and streptoavidin in this region. Thus, the cells having antigens 1703 reacting with the antibodies can be selectively captured.

Figure 18:
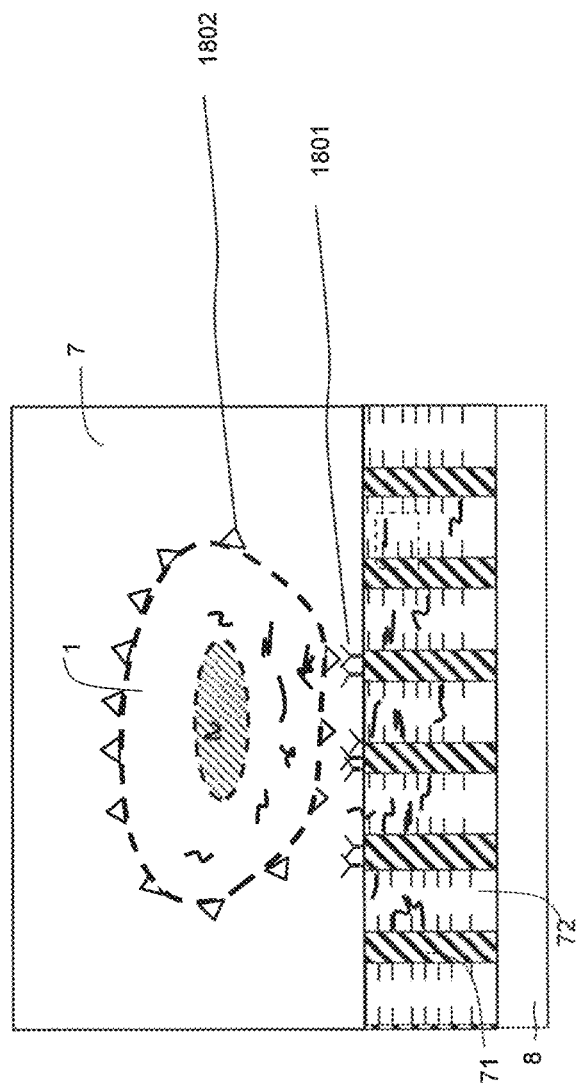
FIG. 18 schematically shows the device for nucleic acid extraction according to an embodiment of the present invention.

An example corresponding to Example 2 (FIG. 7) is shown. As shown in FIG. 18, antibodies are immobilized in a region 1801 for cell trapping (capture) on the porous array sheet 71, so that a cell trapping section capable of capturing cells having antigens 1802 reacting with the antibodies is formed. In order to immobilize antibodies to particular positions, biotinylated antibodies were introduced in amounts of about several tens of pl each with the use of an inkjet printer head. Since the entire device surface is coated with streptoavidin by the method described in Example 3, antibodies would be immobilized selectively in particular regions.

Example 5

Figure 19:
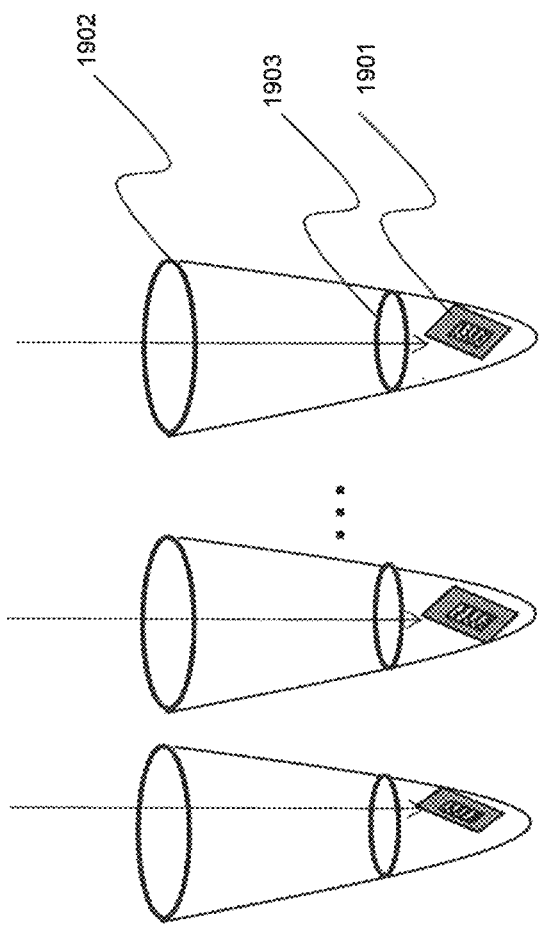
FIG. 19 schematically shows the method of treatment conducted with the use of the device for nucleic acid extraction according to an embodiment of the present invention.

In Examples 1 to 4, a process of 2nd strand formation (steps shown in FIG. 2(*d*) to (*e*) and FIG. 8(*c*) to (*d*)) and a process of PCR amplification (steps shown in FIG. 2(*f*) and FIG. 8(*e*)) are implemented in the apparatus shown in FIG. 5, FIG. 10, FIG. 11, or FIG. 12. In Example 5, however, the entire device for nucleic acid extraction 1901 or a plurality of parts divided from the device for nucleic acid extraction are inserted into a resin tube 1902 (e.g., a 0.2-ml or 1.5-ml tube that is generally used) or a 96-well or 384-well plate as shown in FIG. 19, and a reagent 1903 necessary for 2nd strand synthesis and PCR amplification may be introduced into the tube. Such constitution enables a user to freely modify the conditions for implementing the relevant processes. In addition, a cell recognition tag and a molecule recognition tag can be inserted into a terminus opposite from the position indicated in Examples 1 to 4 by conducting 2nd strand synthesis and subsequent reactions in the tube.

All publications, patents, and patent applications cited herein are incorporated herein by reference in their entirety.

INDUSTRIAL APPLICABILITY

According to the present invention, biomolecule quantification, sequence determination, and molecule identification can be performed for many cultured cells, many immunocytes, cancer cells (in blood), and other cells. Thus, the conditions of cells and the amounts of such cells existing in organisms can be assayed. The present invention enables early diagnosis of cancer and assay of the heterogeneity of iPS cells.

DESCRIPTION OF NUMERAL REFERENCES

1: Cell
2: Cell trapping section
3: Fluid channel
4: Nucleic acid trapping section
5: Fluid channel
6: Planar substrate
7: Upper reaction region
8: Lower reaction region

The invention claimed is:
1. A device for nucleic acid extraction comprising:
an upper reaction region comprising a cell inlet, an upper inlet, and an upper outlet;
a cell trapping section for immobilizing a single cell;
a fluid channel in which an extraction solution for extracting a nucleic acid from the cell flows downward through the cell trapping section;
a nucleic acid trapping section connected to the cell trapping section via the fluid channel and located downstream of the cell trapping section, the nucleic acid trapping section being capable of immobilizing the extracted nucleic acid;

a fluid channel that discharges the solution after nucleic acid extraction from the nucleic acid trapping section in a direction opposite from the cell trapping section; and a porous array sheet with a pore that connects the nucleic acid trapping region to a lower reaction region, wherein the lower reaction region comprises a lower outlet, wherein the cell trapping section, the two fluid channels, and the nucleic acid trapping section are paired in a vertical direction and a plurality of the pairs are arranged in a planar direction, and wherein the nucleic acid trapping section comprises a DNA probe for nucleic acid trapping, and the DNA probe comprises a cell recognition tag sequence.

2. The device for nucleic acid extraction according to claim 1, wherein the nucleic acid trapping section comprises beads on which the DNA probe for nucleic acid trapping is immobilized.

3. The device for nucleic acid extraction according to claim 2, wherein the DNA probe for nucleic acid trapping comprises a sequence for identifying a position on a chip.

4. The device for nucleic acid extraction according to claim 2, wherein the DNA probe for nucleic acid trapping comprises separate sequences for the trapped nucleic acid molecules.

5. The device for nucleic acid extraction according to claim 4, wherein the upper inlet introduces an enzyme for reverse transcription of RNA trapped by the nucleic acid trapping section.

6. The device for nucleic acid extraction according to claim 1, wherein the nucleic acid trapping section comprises a porous membrane comprising the DNA probe for nucleic acid trapping immobilized on pores.

7. The device for nucleic acid extraction according to claim 1, wherein the cell trapping section comprises a substance immobilized thereon that chemically binds to a substance on a cell surface.

8. The device for nucleic acid extraction according to claim 1, wherein a region immediately downstream of the cell trapping section is made of an optically transparent material.

9. The device for nucleic acid extraction according to claim 1, wherein the nucleic acid trapping section is provided in a region immediately downstream of the cell trapping section.

10. The device for nucleic acid extraction according to claim 1, wherein the nucleic acid trapping section is provided in a region other than the region immediately downstream of the cell trapping section.

11. An apparatus for nucleic acid treatment, comprising: the device for nucleic acid extraction according to claim 1; and wherein the upper inlet introduces a reagent for constructing a cDNA library into the device for nucleic acid extraction.

12. An apparatus for nucleic acid treatment, comprising: the device for nucleic acid extraction according to claim 1; a reagent for constructing a cDNA library; and wherein the upper inlet introduces the reagent for nucleic acid amplification into the device for nucleic acid extraction.

13. An apparatus for nucleic acid treatment, comprising: the device for nucleic acid extraction according to claim 1; and a microscope section for observing cells trapped by the cell trapping section under a differential interference microscope, phase contrast microscope, Raman microscope, or Coherent Raman microscope.

14. A method for extracting a nucleic acid from a cell using a device for nucleic acid extraction comprising an upper reaction region comprising a cell inlet, an upper inlet, and an upper outlet;

a cell trapping section for immobilizing a single cell;

a fluid channel in which an extraction solution for extracting a nucleic acid from the cell flows downward through the cell trapping section;

a nucleic acid trapping section connected to the cell trapping section via the fluid channel and located downstream of the cell trapping section, the nucleic acid trapping section being capable of immobilizing the extracted nucleic acid;

a fluid channel that discharges the solution after nucleic acid extraction from the nucleic acid trapping section in a direction opposite from the cell trapping section; and a porous array sheet with a pore that connects the nucleic acid trapping region to a lower reaction region, wherein the lower reaction region comprises a lower outlet, wherein the cell trapping section, the two fluid channels, and the nucleic acid trapping section are paired in a vertical direction and a plurality of the pairs are arranged in a planar direction, and wherein the nucleic acid trapping section comprises a DNA probe for nucleic acid trapping, and the DNA probe comprises a cell recognition tag sequence, the method comprising:

bringing cells into contact with the cell trapping section so as to allow the cell trapping section to trap each cell;

allowing the extraction solution for extracting the nucleic acid from the cell to flow downward through the cell trapping section in the fluid channel;

immobilizing the extracted nucleic acid to the nucleic acid trapping section via the DNA probe comprising the cell recognition tag sequence; and discharging the solution after nucleic acid extraction from the nucleic acid trapping section in the direction opposite from the cell trapping section through the fluid channel.

* * * * *